(12) United States Patent
Umstadter et al.

(10) Patent No.: US 7,321,604 B2
(45) Date of Patent: Jan. 22, 2008

(54) ULTRA-SHORT WAVELENGTH X-RAY SYSTEM

(75) Inventors: Donald Umstadter, Ann Arbor, MI (US); Fei He, Ann Arbor, MI (US); Yue-Ying Lau, Potomac, MD (US)

(73) Assignee: The Regents of the University of Michigan, Ann Arbor, MI (US)

(*) Notice: Subject to any disclaimer, the term of this patent is extended or adjusted under 35 U.S.C. 154(b) by 455 days.

(21) Appl. No.: 10/752,604

(22) Filed: Jan. 7, 2004

(65) Prior Publication Data

US 2005/0147147 A1 Jul. 7, 2005

(51) Int. Cl.
*H01S 3/00* (2006.01)
*H01S 3/09* (2006.01)
(52) U.S. Cl. .............................. 372/2; 372/73
(58) Field of Classification Search ............... 372/2, 372/73
See application file for complete search history.

(56) References Cited

U.S. PATENT DOCUMENTS

| 4,727,551 | A | * | 2/1988 | Scharlemann ............... 372/2 |
| 5,198,674 | A | | 3/1993 | Underwood |
| 5,353,291 | A | | 10/1994 | Sprangle et al. |
| 5,541,944 | A | * | 7/1996 | Neil ........................... 372/2 |
| 5,606,588 | A | | 2/1997 | Umstadter et al. |
| 5,637,966 | A | | 6/1997 | Umstadter et al. |
| 5,789,876 | A | | 8/1998 | Umstadter et al. |
| 5,892,810 | A | | 4/1999 | Sprangle et al. |
| 6,137,811 | A | * | 10/2000 | Sprangle et al. ........... 372/2 |
| 6,332,017 | B1 | | 12/2001 | Carroll et al. |
| 6,333,966 | B1 | * | 12/2001 | Schoen .................... 378/119 |
| 6,624,880 | B2 | | 9/2003 | Sandström et al. |

OTHER PUBLICATIONS

A. Gover and P. Sprangle. "A Unified Theory of Magnetic Bremsstrahlung, Electrostatic Bremsstrahlung, Compton-Raman Scattering, and Cerenkov-Smith-Purcell Free-Electron Lasers." IEEE Journal of Quantum Electronics, QE-17:1196, 1981.
D. Umstadter. "Laser-driven x-ray sources." 2003 Yearbook in Science and Technology. McGraw-Hill, New York, 2003.
E. Jerby and A. Gover. "Investigation of the Gain Regimes and Gain Parameters of the Free Electron Laser Dispersion Equation." IEEE Journal of Quantum Electronics, QE-21:1041, 1985.
E. S. Sarachik and G. T. Schappert. "Classical Theory of the Scattering of Intense Laser Radiation by Free Electrons." Phys. Rev. D, 1:2378, 1970.

(Continued)

*Primary Examiner*—Armando Rodriguez
(74) *Attorney, Agent, or Firm*—Harness, Dickey & Pierce, P.L.C.

(57) ABSTRACT

A method and apparatus to generate a beam of coherent light including x-rays or XUV by colliding a high-intensity laser pulse with an electron beam that is accelerated by a synchronized laser pulse. Applications include x-ray and EUV lithography, protein structural analysis, plasma diagnostics, x-ray diffraction, crack analysis, non-destructive testing, surface science and ultrafast science.

29 Claims, 8 Drawing Sheets

OTHER PUBLICATIONS

F. He, Y. Y. Lau, D. P. Umstadter, and R. Kowalczyk. "Backscattering of an Intense Laser Beam by an Electron." Phys. Rev. Lett., 90:055002, 2003.

F. He, Y. Y. Lau, D. P. Umstadter, and T. Strickler. "Phase dependence of Thomson scattering in an ultraintense laser field." Physics of Plasmas, 9:4325, 2002.

M. I. K. Santala, Z. Najmudin, E. L. Clark, M. Tatarskie, K. Krushelnick, A. E. Dangor, V. Malka, J. Faure, R. Allott, and R. J. Clarke. "Observation of a Hot High-Current Electron Beam from a Self-Modulated Laser Wakefield Accelerator." Phys. Rev. Lett., 86:1227, 2001.

M. M. Kekez. "Simple sub-50-ps rise-time high voltage generator." Rev. Sci. Instr., 62:2923, 1991.

M. Zolotorev. "Laser driven attosecond SASE X-ray FEL." Nuclear Instr. and Methods in Phys. Research A, 483:445, 2002.

P. Catravas, E. Esarey and W. P. Leemans. "Femtosecond x-rays from Thomson scattering using laser wakefield accelerators." Meas. Sci. Technol. 12:1828, 2001.

R. Wagner, S. Y. Chen, A. Maksimchuk, and D. Umstadter. "Electron Acceleration by a Laser Wakefield in a Relativistically Self-Guided Channel." Phys. Rev. Lett., 78:3125, 1997.

S. Banerjee, A. R. Valenzuela, R. C. Shah, A. Maksimchuk, and D. Umstadter. "High harmonic generation in relativistic laser-plasma interaction." Physics of Plasmas, 9:2399, 2002.

S. Banerjee, A. R. Valenzuela, R. C. Shah, A. Maksimchuk, and D. Umstadter. "High-harmonic generation in plasmas from relativistic laser-electron scattering." J. Opt. Soc. Am. B, 20, 2003.

S. D. Baton, et al. "Evidence of Ultrashort Electron Bunches in Laser-Plasma Interactions at Relativistic Intensities." Phys. Rev. Lett., 91:105001, 2003.

S. V. Bulanov, F. Pegoraro, A. M. Pukhov, and A. S. Sakharov. "Transverse-Wake Wave Breaking." Phys. Rev. Lett., 78:4205, 1997.

S. V. Mitko, Y. B. Udalov, P. J. M. Peters, V. N. Ochkin, and K. J. Boller. "Generation of powerful electron beams in a dense gas with a dielectric-barrier-diecharge-based cathod." Appl. Phys. Lett., 83:2760, 2003.

S. Y. Chen, A. Maksimchuk, and D. Umstadter. "Experimental observation of nonlinear Thomson scattering." Nature, 396:653, 1998.

T. Sekikawa, T. Kanai, and S. Watanabe. "Frequency-Resolved Optical Gating of Femtosecond Pulses in the Extreme Ultraviolet." Phys. Rev. Lett., 91:103902, 2003.

V. Malka, et al. "Electron Acceleration by a Wake Field Forced by an Intense Ultrashort Laser Pulse." Sciences, 298:1596, 2002.

Y. Salamin and F. M. H. Faisal. "Harmonic generation by superintense light scaterring from relativistic electrons." Phys. Rev. A, 54:4383, 1996.

Y. Y. Lau, F. He, D. Umstadter, and R. Kowalczyk. "Nonlinear Thomson scattering: A tutorial." Physics of Plasmas, 10:2155, 2003.

* cited by examiner

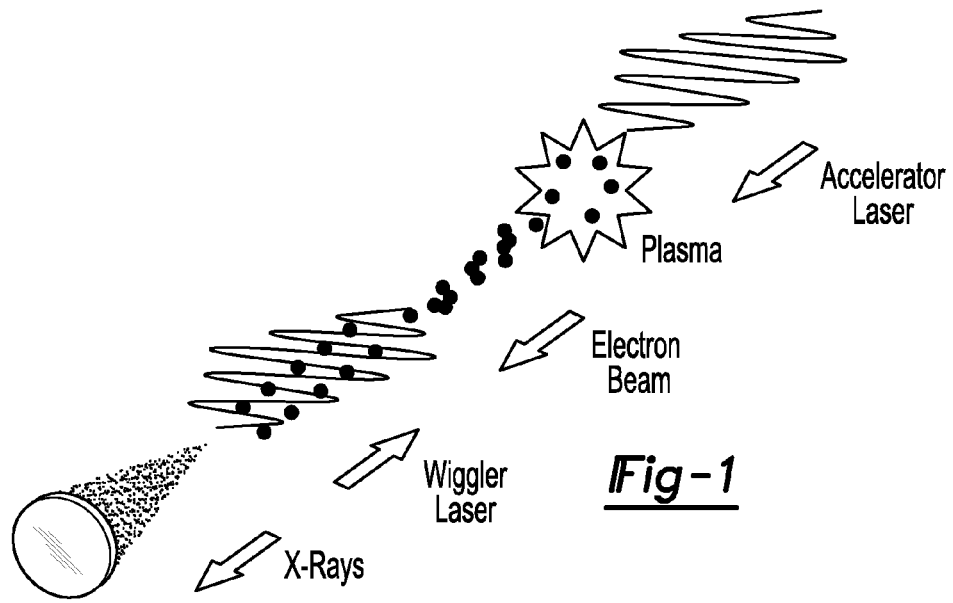
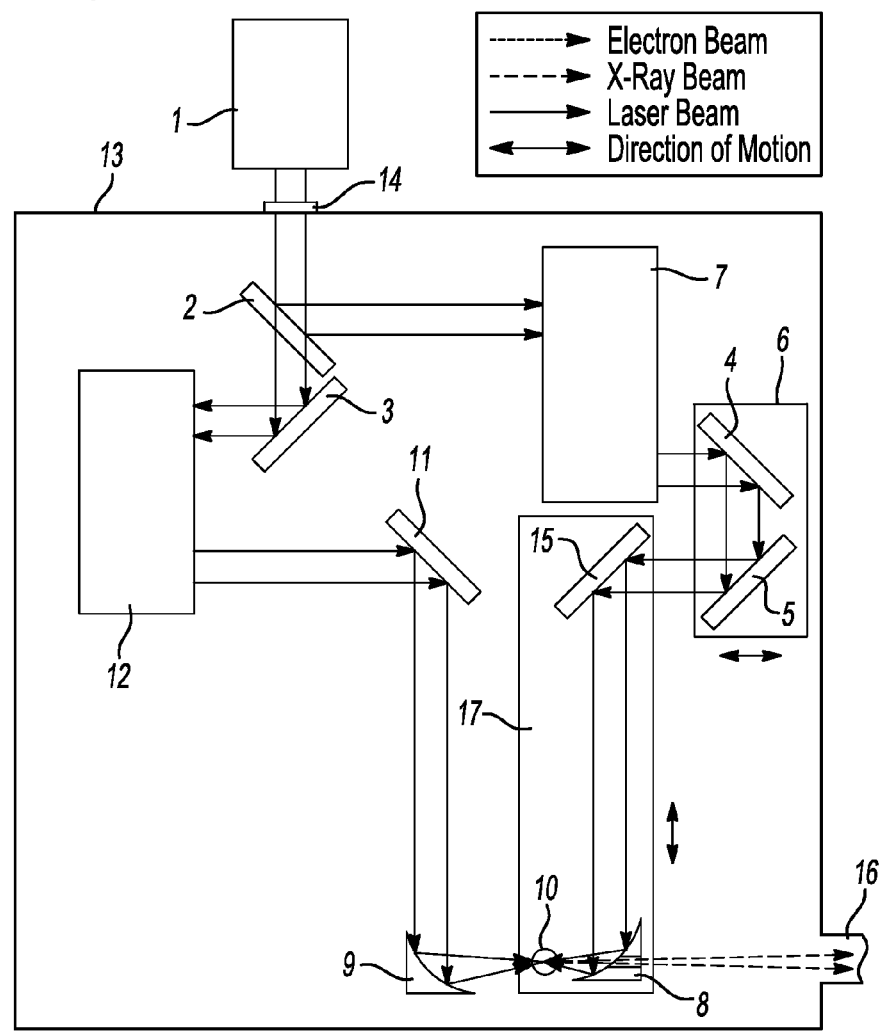

ULTRA-SHORT WAVELENGTH X-RAY SYSTEM

GOVERNMENT'S RIGHT CLAUSE

This invention was made with government support provided by the Department of Energy (Grant No. DE-FG02-96ER14685) and Office of Naval Research (Grant No. N00014-01-1-0849). The government has certain rights in the invention.

FIELD OF THE INVENTION

The present invention relates to ultrashort-pulse-duration and high-power light sources.

BACKGROUND OF THE INVENTION

In order to satisfy the needs of basic research as well as industry, there is currently great interest in coherent, ultrashort-pulse-duration and high-power light sources. In basic research, large (kilometer) x-ray synchrotrons have met some of these needs, but they are extremely expensive, costing hundreds of millions of dollars. Thus, there is a need for an affordable and compact source, having a small enough footprint to fit in a university or industrial research laboratory or factory setting. Additionally, light with shorter pulse durations than are currently produced by synchrotrons are required in order to provide ultrafast time-resolution of transient physical or chemical processes. Perhaps the most important applications of advanced x-ray sources are EUV lithography and protein structural analysis.

In the former case, in order for computer chips to continue their exponential increase in speed for a given size, the next generation of lithography will require features resolution of less than 50 nm, which in turn will require a bright source of light with a wavelength of 13.6 nm. However, current sources at this wavelength are not powerful enough to meet the computer manufacturing industry's requirements.

In the case of protein structural analysis, the primary motivation is to be able to map by use of x-ray diffraction the large number of proteins (over one million) as has been done for genes (30,000) in the past. Obtaining this information is important because proteins direct most biological functions. Because of the size of the molecules involved, there is a great need to be able to resolve even smaller features than in lithography, 1 nm or less.

SUMMARY OF THE INVENTION

The present invention addresses the need for a highly collimated and coherent source to make it possible to better interpret structures by having a well-defined diffraction phase. Also, a short pulse is desirable in order to obtain the structural information before damage to the sample from the absorption of radiation. For the proteins that can be crystallized, ~$10^{10}$ x-ray photons per shot are sufficient. Such large fluxes are not currently produced by any source small enough to fit on an industrial research laboratory floor.

The invention provides a method and apparatus to generate a beam of coherent light that satisfies all of requirements for uses in lithography and protein analysis, among other applications. It is based on the Thomson scattering of a high-intensity laser pulse with an electron beam that is accelerated by a synchronized laser pulse. In one aspect, a laser-accelerated electron gun is coupled with an electromagnetic wiggler or undulator. A further refinement is the operation of the device in the collective regime by means of the free-electron laser (FEL) mechanism, which increases the coherence of the light as well as increases its power. In order to operate in this collective regime, the invention provides several means by which the output of the laser-driven electron accelerator can be made relatively monoenergetic. Also disclosed are the results of simulations and calculations that confirm the attendant large increase in the x-ray power at the wavelength of interest for EUV lithography, based on the experimentally measured electron beam parameters from a laser-based accelerator. Also disclosed are methods to increase the electron flux and thus the scattered x-ray power. The inclusion of other concepts for decreasing the energy-spread of laser-based accelerators, such as laser injection of electrons (see Umstadter U.S. Pat. No. 5,789,876), increases this power even further. The invention also provides a method for seeding the amplification by the injection of radiation of the desired wavelength from a separate synchronized laser-pumped x-ray source.

The invention provides a method and apparatus to generate short-wavelength radiation by means of Thomson scattering in both the single particle and the collective regime from a laser-driven accelerator using an electromagnetic (laser) wiggler or undulator. In a related aspect, the invention provides a method to increase the amplification of short-wavelength radiation by creating a lower emittance beam of electrons from a laser-driven accelerator; and creating a more monoenergetic beam of electrons from a laser-driven accelerator.

Other features include: a method to tune the wavelength of short-wavelength radiation by varying the energy of a laser-accelerated beam of electrons; a method to overlap a laser beam with an electron beam in order to increase the amplification of short-wavelength radiation; a method to vary the wavelength of short-wavelength radiation by varying the energy of laser accelerated electrons; a method to satisfy phase-matching for the generation of short-wavelength radiation by varying the angle of laser accelerated electrons with respect to the angle of a scattering laser beam; and a method to change the pulse duration of short-wavelength radiation by varying the angle of laser accelerated electrons with respect to the angle of a scattering laser beam.

Still other features include: a method to increase the flux of short-wavelength radiation by increasing the flux of laser accelerated electrons; and a method to increase the flux of short-wavelength radiation by varying the pulse duration of a scattering laser beam.

Further features include: a method to increase the flux and/or coherence of short-wavelength radiation by seeding a laser-driven FEL (electromagnetic wiggler) with a high-order harmonic radiation from the interaction of lasers with solids, liquids, gases or plasmas; a method to increase the flux and/or coherence of short-wavelength radiation by seeding a laser-driven FEL with continuum Thomson scattered radiation by seeding a laser-driven FEL with radiation from betatron oscillations of electrons driven by lasers propagating in plasma channels.

Finally, the invention includes a method to generate short-wavelength radiation for EUV, XUV or x-ray lithography, and for protein structural analysis.

Systems and apparatus are provided for use in the aforesaid methods.

In view of the foregoing, in general, the invention provides a method for generating electromagnetic radiation comprising producing a group of free electrons, undulating the group of free electrons and causing emission of radiation. Various aspects of producing free electrons includes:

accelerating free electrons by means of an electron beam in a plasma; accelerating free electrons in a plasma; accelerating free electrons by means of a laser in a plasma; where the accelerating is accomplished, at least in part, by plasma wakefield; and where the accelerating is assisted by a DC (direct current) electric field.

The undulating is accomplished by various means, including an electromagnetic laser wiggler and a magnetostatic undulator, among the more preferred variations.

The method of the invention is used to lithographically pattern a substrate comprising generating electromagnetic radiation by the method of the invention and directing the radiation to the substrate. In one variation, the electromagnetic radiation obtained by the method of the invention is directed first to a mask and then to the substrate. In another variation according to the invention, the method for generating electromagnetic radiation is usable in a method to produce data for analysis of defined structures comprising: generating the electromagnetic radiation by the method of invention and directing the radiation to the structure; and then imaging the radiation to a detector. The method of the invention is also usable to produce electromagnetic radiation for analysis of protein structure comprising generating electromagnetic radiation by the method of the invention and directing the radiation to the protein structure and then to a detector.

Other important general features of the invention included the production of radiation at either a fundamental frequency; or where the radiation produced by the method of the invention comprises multiple frequencies that are multiples of a fundamental frequency. Such multiple frequencies are generated by the undulator, characterized by its field strength that is essentially non-sinusoidal.

In a further feature of the method of the present invention, multiple amplifiers are used. This method comprises: generating a first group of free electrons, then separately generating seed radiation; and undulating the first group of free electrons in the presence of the seed radiation, thereby producing first amplified radiation. Then a second group of free electrons is generated, and the second group of free electrons and the first amplified radiation are directed to a second undulator to produce second amplified radiation.

Those skilled in the art will appreciate that multiple amplification with additional free electrons is possible. In this case, the first group of free electrons and seed radiation is generated and an upstream undulator is used, to generate upstream amplified radiation. Then a further group of free electrons is generated, the upstream amplified radiation and the further group of free electrons are directed to a downstream undulator, with repetition of the upstream feed to the downstream undulator, multi-stage amplification for a desired number of stages occurs.

Further in accordance with the earlier described features, free electrons are produced in spatially separate groups having essentially non-overlapping energy ranges. The spatially separate groups of free electrons having the different energy ranges are undulated essentially simultaneously in respective separate undulators to cause emission of radiation at various frequencies.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a schematic diagram illustrating the underlying physical mechanism.

FIG. 2 is a schematic of a system for producing ultra-short wavelength radiation. In this geometry, no electrostatic or magnetostatic filtering is employed, but the electron energy spread is reduced by use of multiple laser beams or a density discontinuity to inject electrons at a prescribed phase.

DETAILED DESCRIPTION OF THE PREFERRED EMBODIMENTS

Figure 3:
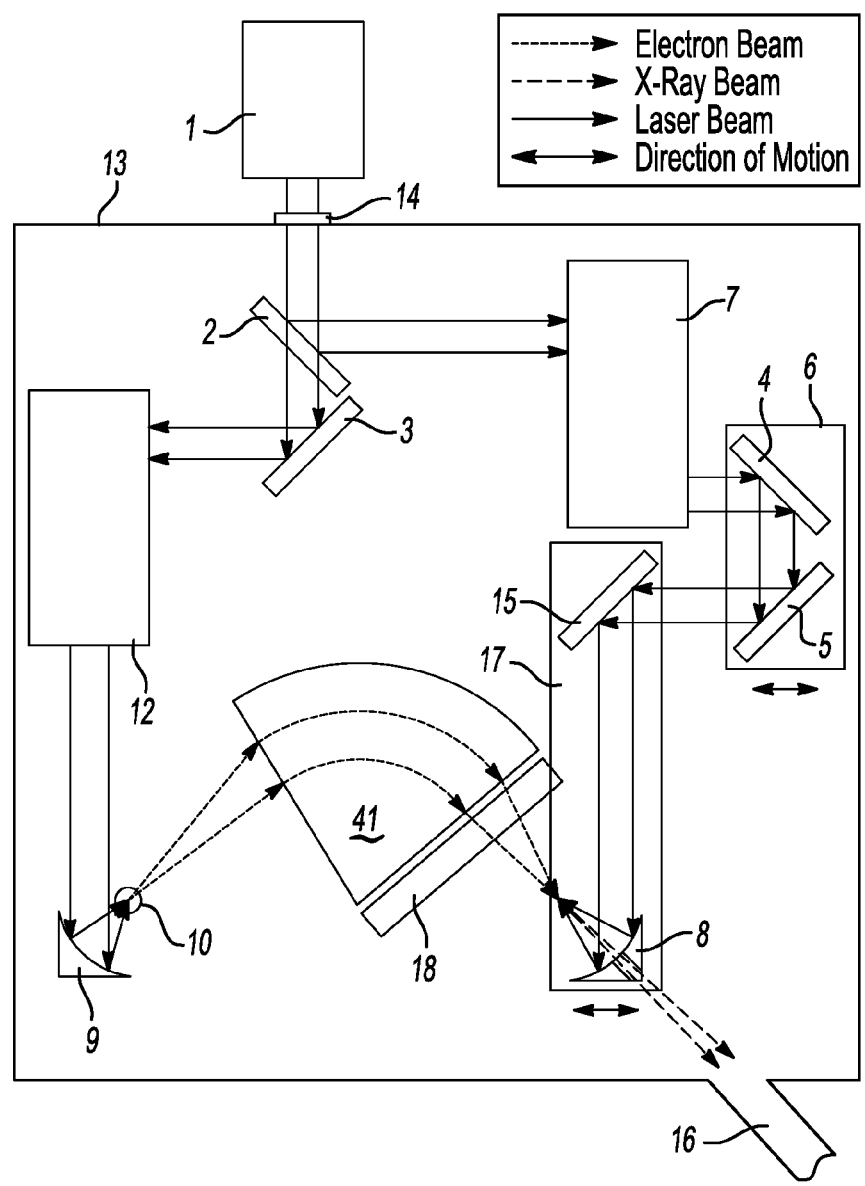
FIG. 3 is a second embodiment of an apparatus for producing ultra-short wavelength radiation. This shows a DQ configuration. A sector magnet is used in conjunction with a quadrupole to reduce the energy spread of the electron beam.

The following description of the preferred embodiment(s) is merely exemplary in nature and is in no way intended to limit the invention, its application, or uses.

Laser-based accelerators currently produce electron beams that are well collimated (less than 1-degree divergence angle) with nanoCoulombs of charge, with sub-picosecond pulse durations and at repetition rates of 10 Hz. They are based on the generation of high amplitude plasma waves by high-power lasers, by one of several mechanisms, such as the self-modulated laser wakefield acceleration mechanism, the resonantly driven wakefield mechanism (see Umstadter U.S. Pat. No. 5,637,966), and the beatwave accelerator mechanism. One important attribute of these optically-driven accelerators as compared to their more conventional radio-frequency based counterparts is that the accelerating gradient (1 GeV/cm) is four orders of magnitude greater. Thus electron energies of 100-million electron volts (MeV) can be achieved in a distance of only 1 mm, as compared with 10 meters. One aspect of their beam quality, the transverse emittance, is found to be comparable, or even lower, than that from a conventional accelerator. However, their longitudinal emittance, or energy spread, is large, almost 100%. Such a large energy spread is reducable by use of magnetic filters or injection methods, such as optical injection (see Umstadter '876) or the use of sharp density gradients. Recent experiments have shown experimentally that Thomson scattering by such a co-propagating electron beam produces a collimated beam of high-order harmonics, also in the direction of the laser light. Thomson scattering from counter-propagating relativistic electron beams (see FIGS. 1 and 2) also results in a Doppler shift, which can further up shift the energy of the scattered light well into the x-ray region of the spectrum. For example, electrons with only 100-MeV energy can boost a 1-eV energy photon to 50 keV. This leads here to an all-optically driven "table-top" hard x-ray source, which is of interest not only as a probe with atomic-scale spatial resolution, but also as a medical diagnostic because of the large penetration of such energetic light through matter. The basic physical mechanism of the invention is as shown in FIG. 1.

FIG. 2, a schematic in greater detail, shows that laser light from a high power laser system 1 enters a vacuum chamber 13 through a glass window 14. Beam splitter 2 divides the beam into two beams. One goes to pulse compressor 12 and the other to delay stage 6 and then on to pulse compressor 7. The pulse compressors are used to adjust the pulse durations of the two laser beams. Both beams are then focused to high laser intensities by off-axis parabolic mirrors 9 and 8. One beam (the pump beam) is focused into a high-pressure gas jet 10 such that a laser wakefield plasma wave is driven to high amplitude, which then accelerates an electron beam to megavolt (MeV) energy. The electron beam is focused to a point that overlaps spatially and temporally with the counterpropagating laser beam focused by off-axis parabolic mirror 8. Thomson scattering, which occurs when the electron beam overlaps with the other high-intensity laser beam (the scattering beam), creates a collimated x-ray beam, which propagates in the same direction to the electron beam. If the electron beam is monoenergetic, then a narrow band x-ray spectrum can be produced. A small hole in off-axis parabolic mirror 8 allows the x-ray beam to pass through the mirror 8 to the exit port 16, leading to the applications chamber. By translating the position of the scanning stage 17, and thus mirror 15 and off-axis parabolic mirror 8, the laser focus can be made to spatially aligned to the electron beam. Temporal overlap between the laser beam and the electron beam is assured by translating delay line 6.

In the case where electron energy is reduced, coherent radiation with significant amplification over the incoherent signal is generated by means of collective bunching of the electrons. This is commonly referred to as the free-electron lasing mechanism. An important feature of the present invention is a method to produce a coherent beam of short-wavelength radiation through the FEL mechanism with lasers acting as both the driver for the accelerator as well as the wiggler or undulator.

There exist other means to generate x-rays, such as with synchrotrons and conventional free-electron lasers (FEL). They rely on conventional (radio-frequency) accelerators to generate an electron beam, but because of their low field gradients (0.1 MeV/cm), they are usually quite large (tens to hundreds of meters in length). Long sets of magnets (tens of meters) are required to wiggle the electrons. Laser-Thomson sources, by contrast, accelerate electrons in mm distances and the electrons are wiggled in a mm long interaction region by the magnetic field of the laser pulse.

The preferred all-optical laser-driven source provides better temporal resolution (femtoseconds instead of tens of picoseconds). This is preferred over a short-pulse x-ray FEL based on radio-frequency accelerators and magnetostatic wigglers, because in each case this will require a 50-GeV energy electron beam conventionally accelerated in a 3-km long tunnel to be passed through a 50-m long set of wiggler magnets. FELs do have the advantage over Thomson sources in that the electrons become tightly bunched, improving coherence and x-ray power. Because of their small footprint, laser-driven Thomson sources and those enhanced by FEL interactions will be much more affordable (less than $1 Million), thus permitting their operation at university, industrial and hospital labs. The all-optical laser-driven source has a sub-millimeter length accelerator and wiggler. The reason that an accelerator and wiggler based on lasers can be so much shorter than one based on a radio-frequency accelerator and a magnetostatic wiggler is that the electromagnetic wiggler wavelength is micron instead of centimeter, and consequently, the energy of the accelerator only needs to be MeV instead of GeV to Doppler shift the scattered radiation to a given short wavelength. Also, the length of a laser accelerator is four orders of magnitude shorter to achieve a given energy compared to a radio-frequency accelerator.

The present invention's simulations and calculations show that significant gain, on the order of 400 times, is achieved by the FEL mechanism at the important wavelength of 13-nm EUV radiation for lithography if the energy spread of the accelerator is reduced to an easily achievable value of a few percent. In the limit of zero emittance, the gain is $10^6$. The energy spread is reduced by one of several methods: phased injection of electrons into the plasma wave or magnetic filtering. The former can be accomplished by means of either optical injection or by a plasma density discontinuity. One feature of the present invention is a method to achieve a plasma density discontinuity by driving a shock in the gas jet, either with the collision of flows from two different jets or one jet and a physical stop to disrupt the flow. Free-electron laser gain results when one of these methods to reduce the electron energy spread were used in the scattering geometry shown in FIG. 2. At the very least, the electron flux increases by one of these methods of injection.

In a further feature, electron energy spread reduction is achieved by means of magnetic filtering. Several methods to reduce the energy spread by means of magnetic filtering and focusing are also described herein. In all cases, the electron beam is dispersed in energy by a dipole magnetic field and focused. If the scattering laser beam is focused to overlap with the electron focus, but the electrons are dispersed spatially at their focus, then the laser beam interacts with only a narrow range of electron energies at any particular focal position. If the position of the laser focus is scanned along the dispersion direction, then the energy of the scattered x-rays is varied, making this a tunable source.

For instance, in one embodiment of the invention, a sector electro magnet is used to both disperse and focus the electrons, as shown in FIG. 3. Laser light from a high power laser system 1 enters a vacuum chamber 13 through a glass window 14. Beam splitter 2 divides the beam into two beams. One goes to pulse compressor 12 and the other to delay stage 6 and then on to pulse compressor 7. The pulse compressors are used to adjust the pulse durations of the two laser beams. Both beams are then focused to high laser intensities by off-axis parabolic mirrors 9 and 8.

One beam (the pump beam) is focused into a high-pressure gas jet 10 such that a laser wakefield plasma wave is driven to high amplitude, which then accelerates an electron beam to megavolt (MeV) energy. The electron beam is energy dispersed by sector magnet 41 and focused to a point that overlaps spatially and temporally with the counterpropagating laser beam focused by off-axis parabolic mirror 8. Thomson scattering and those enhanced by FEL interactions, which occurs when the monoenergetic electron beam overlaps with the other high-intensity laser beam (the scattering beam), creates a collimated, coherent and monoenergetic x-ray beam, which propagates in the opposite direction to the laser beam. A small hole in off-axis parabolic mirror 8 allows the x-ray beam to pass through the mirror 8 to the exit port 16, leading to the applications chamber. By translating the position of the scanning stage 17, and thus mirror 15 and off-axis parabolic mirror 8, the laser focus can be made to spatially overlap with different regions of the electron beam, which contain different energy components, thereby tuning the scattered x-ray energy. Temporal overlap between the laser beam and the electron beam is assured by translating delay line 6. While this has the advantage of simplicity, it unfortunately suffers from the fact that it provides focusing in only one dimension. Because there is no vertical focusing, the number of electrons that reach the interaction region will not be as high as it would be in the case of focusing in both dimensions. Thus, a further improvement is to add a quadrupole magnet 18 to focus the beam in the one dimension that the sector magnet does not, as shown in FIG. 3. Alternatively, three quadrupole magnets, instead of a single magnet, are arranged to follow a sector magnet to focus the beam.

Figure 4:
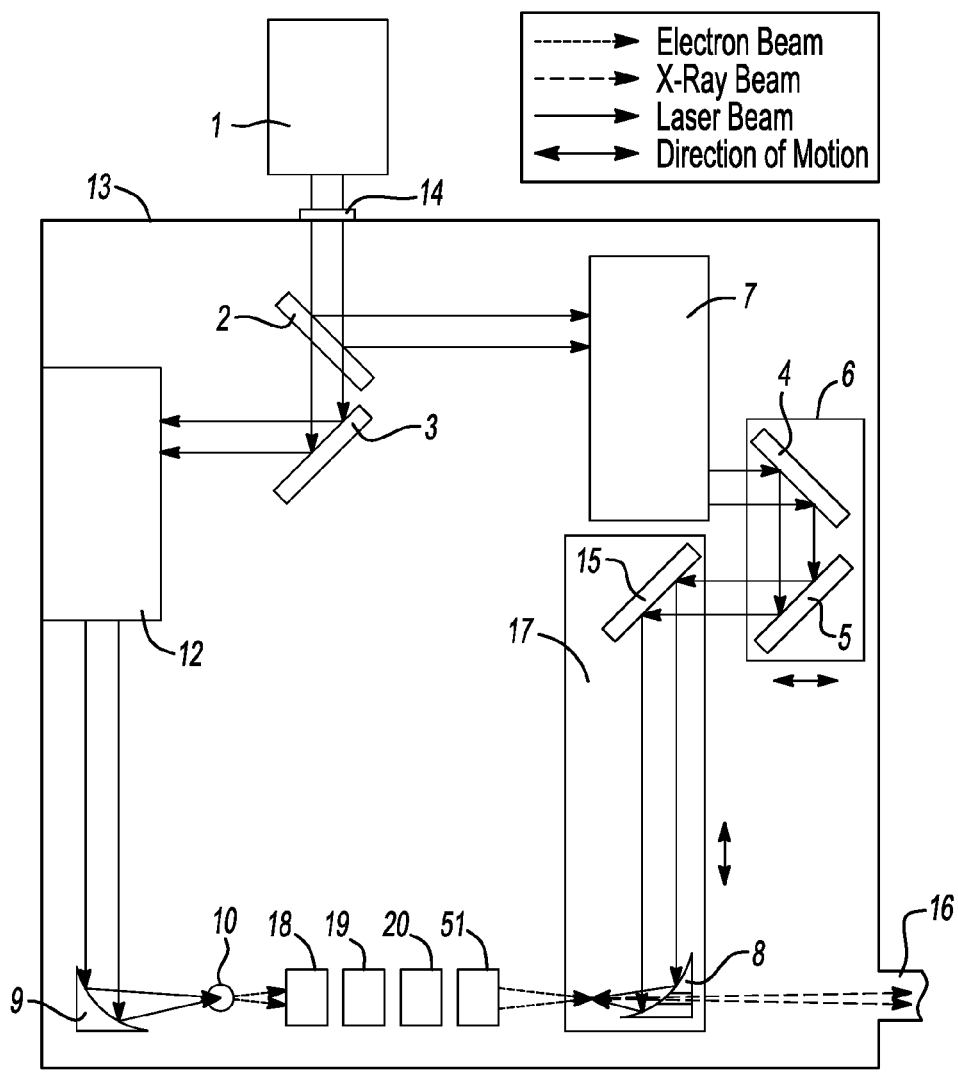
FIG. 4 is a third embodiment of an apparatus for producing ultra-short wavelength radiation. This shows a QQQD configuration. In this case, the energy spread of the electron beam is reduced and the electron source is imaged to the interaction region by use of three quadrupole magnets followed by a dipole.

A further alternative arrangement is shown in FIG. 4, where the beam is focused and dispersed by means of three quadrupole electromagnets followed by a dipole electromagnet. The electron beam source is then imaged in both dimensions to the scattering laser beam's focal point. Laser light from a high power laser system 1 enters a vacuum chamber 13 through a glass window 14. Beam splitter 2 divides the beam into two beams. One goes to pulse compressor 12 and the other to delay stage 6 and then on to pulse compressor 7. The pulse compressors are used to adjust the pulse durations of the two laser beams. Both beams are then focused to high laser intensities by off-axis parabolic mirrors 9 and 8. One beam (the pump beam) is focused into a high-pressure gas jet 10 such that a laser wakefield plasma wave is driven to high amplitude, which then accelerates an electron beam to megavolt (MeV) energy. The electron beam is energy dispersed and focused—by a combination of magnets (a QQQD configuration), three quadrupole magnets 18, 19, 20 and a dipole magnet 51—to a point that overlaps spatially and temporally with the counterpropagating laser beam focused by off-axis parabolic mirror 8. Thomson scattering and those enhanced by FEL interactions, which occurs when the monoenergetic electron beam overlaps with the other high-intensity laser beam (the scattering beam), creates a collimated, coherent and monoenergetic x-ray beam, which propagates in the opposite direction to the laser beam. A small hole in off-axis parabolic mirror 8 allows the x-ray beam to pass through the mirror 8 to the exit port 16, leading to the applications chamber. By translating the position of the scanning stage 17, and thus mirror 15 and off-axis parabolic mirror 8, the laser focus can be made to spatially overlap with different regions of the electron beam, which contain different energy components, thereby tuning the scattered x-ray energy. Temporal overlap between the laser beam and the electron beam is assured by translating delay line 6.

Figure 5:
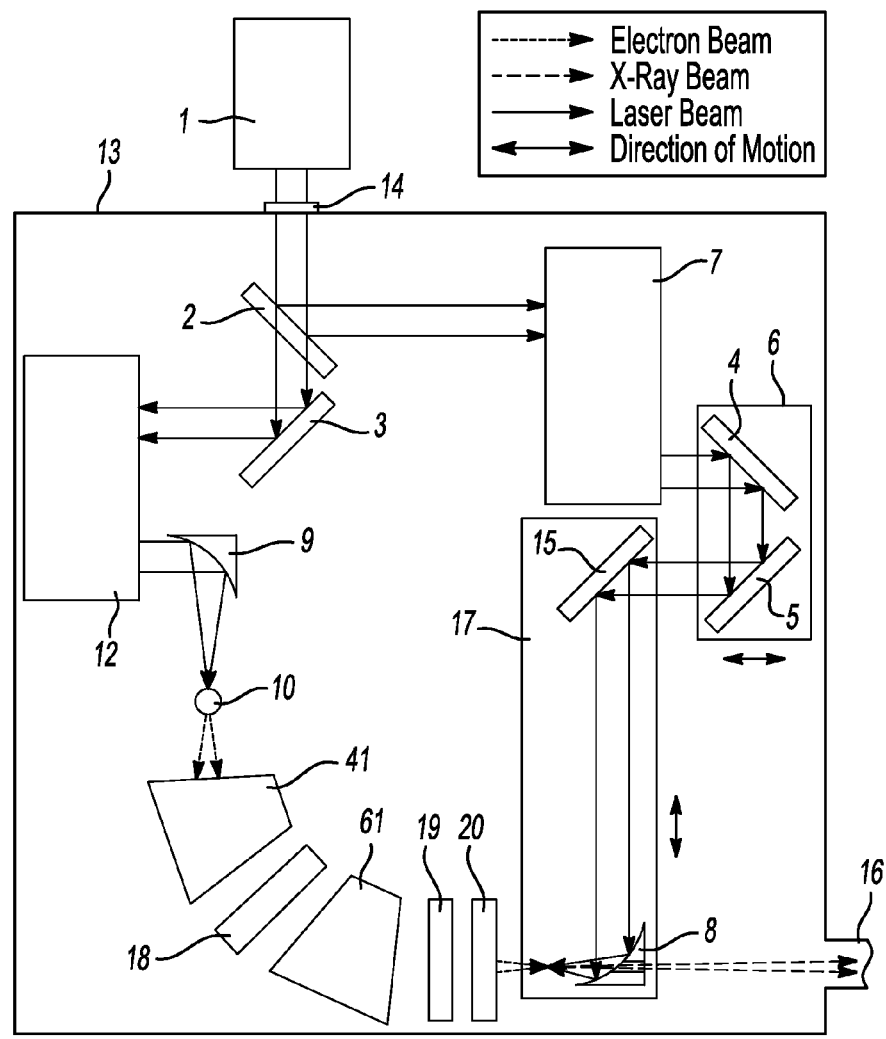
FIG. 5 is a fourth embodiment of an apparatus for producing ultra-short wavelength radiation. This shows a DQDQQ configuration. In this case, the energy spread of the electron beam is reduced and the electron source is imaged to the interaction region by use of a quadrupole magnet between two dipoles followed by two more quadrupoles.

A different exemplary magnetic configuration (DQDQQ) (41, 18, 61, 19, 20) for reducing the energy spread of, and imaging, the electrons is known as U.S. Pat. No. 5,198,674 (Underwood) and is shown in FIG. 5.

With any of the chromatic magnetic filtering systems described above, electrons with slightly different energy ranges are focused to slightly different spatial locations. They are undulated separately and simultaneously, during the same duty cycle of the laser, to generate electromagnetic radiation with different wavelengths. This is a convenient feature when several different wavelengths are used for different applications simultaneously or for the same application; for instance, for improved contrast imaging when one wavelength is above and one is below an atomic absorption edge.

In all cases, the angle of incidence of the scattering laser beam is able to be varied with respect to the direction of propagation of the electron beam, providing another independent parameter with which to meet the phase matching requirements.

Figure 6:
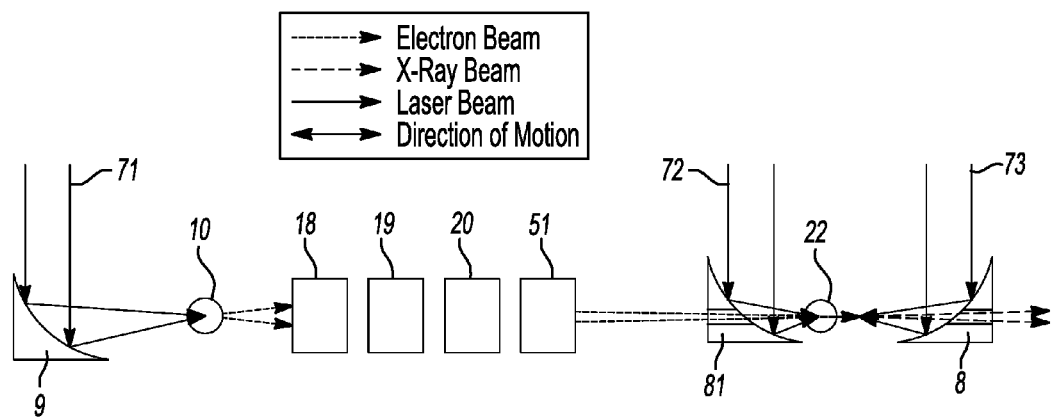
FIG. 6 is a fifth embodiment of an apparatus for producing ultra-short wavelength radiation. This shows an oscillator-amplifier configuration. The components are the same as in FIG. 4, but another synchronized laser beam has been added, a harmonics pump laser beam, which is split off with a beam splitter and independently delayed by a delay line in similar fashion to the amplifier pump beam. The optics used to split the beam and delay it, along with those used to do the same for the other two laser beams from FIG. 4 are not shown. This beam is focused to a gas jet by a parabolic mirror with a hole in it, through which the electron beam passes. The radiation from the gas jet seeds the amplifier. The same QQQD configuration of FIG. 4 is used to reduce the energy spread of the electrons, but only the dipole magnet is shown.
Figure 7:
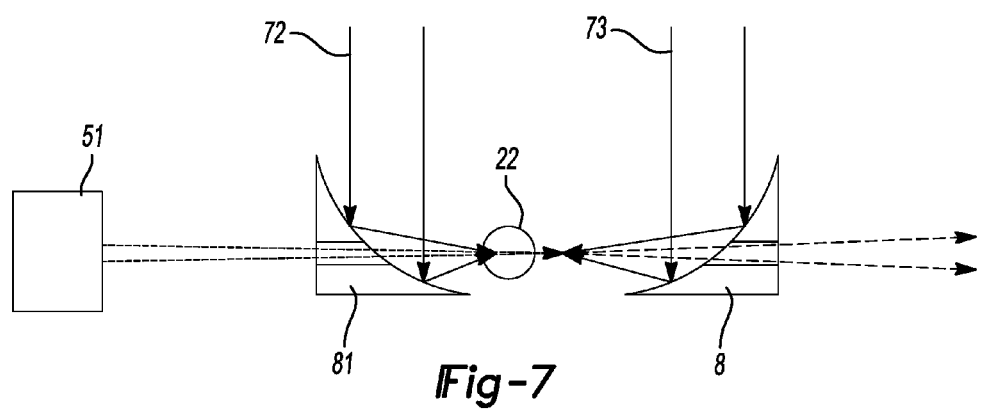
FIG. 7 shows an enlarged version of final optics from FIG. 6. The oscillator-amplifier configuration is enlarged.
Figure 8:
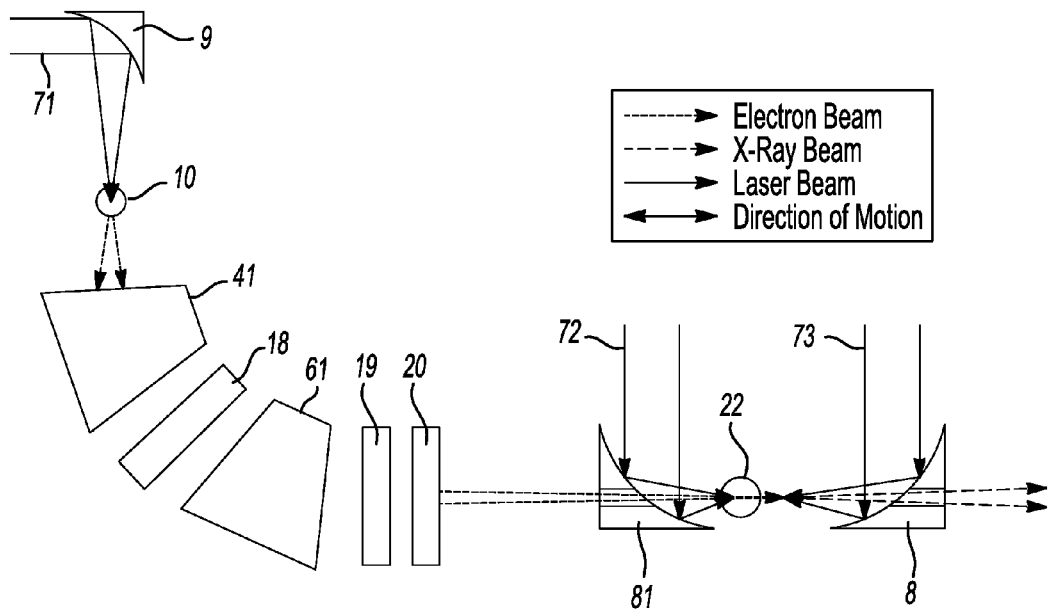
FIG. 8 shows another oscillator-amplifier configuration. The components are the same as in FIG. 6, but a DQDQQ configuration of FIG. 5 is used to reduce the energy spread of, and image, the electrons.

In yet another aspect, the present invention provides an oscillator-amplifier configuration and a method to increase the absolute amplified power and coherence of the x-ray beam, which is an optical analogue to a travelling wave tube with distributed gain. Here, the same principles discussed above are used to create amplified gain, called the amplifier, but rather than amplify a signal spontaneously from the level of noise, the amplifier is seeded with a signal generated by an "oscillator." This injected signal could be either incoherent or coherent radiation that is generated in a gas jet. In the former case, it could be incoherent Thomson scattering, and in the latter case, it could be coherent harmonics generated from bound electrons in either gases or clusters interacting with low-intensity laser light (below the ionization threshold). For instance, the ninth harmonic of the 800 nm light could easily produce 90-nm wavelength light, which is of interest for EUV lithography. By varying the wavelength of the fundamental frequency of the driver, the wavelength of the harmonic can be varied. Injecting seed radiation will increase the final amplified signal as well as the coherence of the light. FIGS. 6, 7 and 8 show schematics of various arrangements for seeding the amplifier.

In the schematic of the oscillator-amplifier configuration, shown in FIG. 6, the components are mostly the same as those shown in FIG. 4, except that another synchronized laser beam has been added, a harmonics pump laser beam 72, which is split off with a beam splitter and independently delayed by a delay line in similar fashion to the amplifier pump beam 71. The optics used to split the beam and delay it, along with those used to do the same for the other two laser beams from FIG. 4 are not shown. This beam is focused to a gas jet 22 by a parabolic mirror 81 with a hole in it, through which the electron beam (coming from 51) passes. The seed pulse of radiation, from the gas jet (22), seeds the amplifier. The same QQQD configuration of FIG. 4 is used to reduce the energy spread of the electrons, but only the dipole magnet (51) is shown.

FIG. 8 show an oscillator amplifier just like FIG. 6 except that the DQDQQ configuration of FIG. 5 is used to filter the electron energy, instead of the DQQQ of FIG. 4. In FIG. 8, the electron beam leaving the laser magnet of the filtering section, in this case the quadropole 20, is focused to the undulator region to the right of gas jet 22, where also the seed radiation and the amplifier pump radiation 73 are focused.

FIG. 7 shows an enlarged version of the seed generation and amplifier sections from FIG. 6. It can be seen that the amplifier pump laser 73 is focused to the undulator region, just to the right of the target, which in this case is a gas jet 22 that provides the medium used to produce the seed radiation. By locating the undulator region close in proximity to the source of the seed radiation, the intensity of the latter is not reduced by divergence that is caused by diffraction. The seed radiation could be produced by harmonic or continuum emission in gases, clusters or plasmas.

Figure 9:
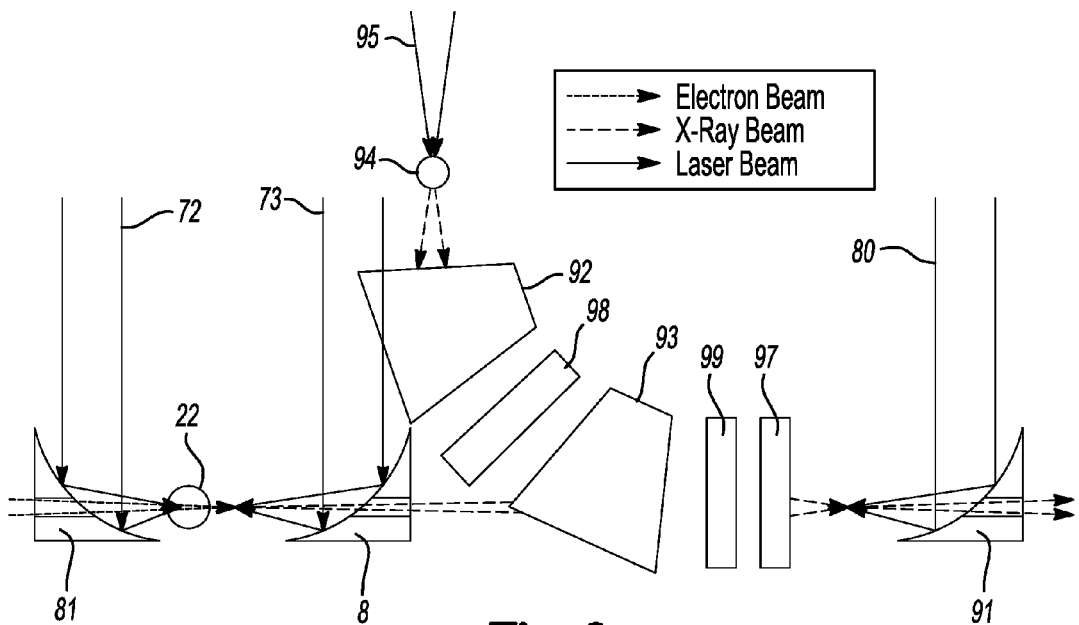
FIG. 9 shows a dual amplifier configuration. A second amplifier stage is added, in which a second electron beam and a second pump laser are used, after the seeding stage and the first amplifier of FIG. 6.

In still another aspect, the present invention provides multi-amplifier configuration. In a dual amplifier, the output of the first amplifier is amplified again by a second amplifier, as shown in FIG. 9. The x-ray signal is transported between amplifiers, or between the seed source and the first amplifier, by means of x-ray optics, such as zone plates, curved mirrors or poly-capillary fiber array waveguides. Shown in FIG. 9 is the seed stage, comprising the seeding pump laser 72, producing a seed pulse from gas jet 22, which is amplified by the electron beam that comes from the left of, and passes through a hole in, parabolic mirror 81, and is focused to the amplifier region, just to the right of 22. Amplifier pump beam 73 is focused to the same location, amplifying the seed pulse. The amplified radiation pulse then is transported through the hole in parabola 8 to the second amplifier region, at the focus of the second amplifier pump beam 80, which is focused by parabola 91. The electron beam that is generated in gas jet 94 by the second stage electron pump laser 95 and filtered by the DQDQQ magnets (92, 98, 93, 99, and 97) is focused to the same location as pump beam 80 and the radiation from the first amplifier. The radiation amplified by the second amplifier is transported to the right, through the hole in parabola 91, to the application region.

Electromagnetic radiation can be generated both at the fundamental wavelength, as described above, as well as the harmonics of the radiation. The harmonics are generated at several different wavelengths, separated by multiples of a fixed amounts, during undulation due to nonlinear interaction. These harmonics produce shorter wavelength radiation for a given electron energy than would the generation of the fundamental alone. The harmonic content increases with the wiggler field strength. This trend does not continue beyond to a certain point for values of the normalized vector potential above a few. This is an alternative means to the Doppler shift of generating shorter wavelength radiation.

The ideal pump laser systems are high average power (10-1000 W) solid-state laser-pumped or diode-pumped lasers. An example of the former would be a frequency doubled YAG-pumped Ti:sapphire system operating at 1-100 Hz duty cycle, 30-1000-fs pulse duration, 10-100-TW peak power, 1-1000 joules of energy per pulse, and 800-nanometer wavelength. Alternatively, a diode-pumped or Alexandrite-pumped amplifier composed of Yb:FSA or Yb:Glass or Yb:YAG. Last, gas lasers, such as $CO_2$ lasers, that produce short pulses by means of optical switching are usable in and system of the invention. In any case, the laser system might be built for less than $1 Million and fit into a room that is only 25 $m^2$.

Such large gains may allow the invention to be used in conjunction with a high-power laser to achieve sufficient power in the EUV spectral region to be suitable for EUV lithography.

For instance, 40 W at 13.5 nm, the current design goal for EUV lithography, is reachable with a 1.1 kW laser system pumping a laser-driven FEL operating with the maximum theoretical conversion efficiency from optical to x-ray radiation, which is the saturation efficiency of the amplifier, 3.6%. To avoid the problems associated with the beam's coherence for lithography applications, standard techniques to decohere the beam, such as random phase plates, is employed. Another advantage of the laser-driven Thomson source as compared with current sources based on xenon clusters is that debris is eliminated because the target that generates electron beam is well separated from both the region where the XUV radiation is generated and thus where the expensive XUV optics are located. The electron beam that propagates in the direction of the XUV radiation is able to be deflected with a simple dipole magnet. It should be noted that with current sources based on xenon clusters 40% of the laser energy goes to energetic ions that are more difficult to deflect and can contaminate the expensive x-ray optics. Moreover, with the present method, the XUV radiation is produced in a narrow beam rather than into a solid angle of $\sin^2(\theta)$, as in the case of current sources based on xenon clusters; thus the radiation can be transported to the XUV collection optics without significant loss of power.

Further reductions in the energy spread will allow gain in the x-ray region for use in protein structural analysis by means of x-ray diffraction. The increased coherence from seeding should make this source as bright and coherent as the much larger and more expensive synchrotrons. For protein structural analysis with proteins that can be crystallized, $10^{10}$ x-ray photons at or below 1 nm wavelength are required and are produced in a single shot with a conversion efficiency of only $10^{-6}$, assuming 10-J energy in the pump lasers. As discussed below, such conversion efficiencies are easily attained. It is also shown that the most demanding requirements on the x-ray brightness ($10^{13}$ photons/$mm^2 \cdot mrad^2 \cdot s \cdot 0.1\%$ BW) for microcrystal data measurements with small mosaic spreads are able to be met with a laser-based FEL. The high peak power of the source has an important advantage over conventional sources—such as synchrotrons, which have high average power but low peak power—because radiation damage of the protein and surrounding media favors the acquisition of the data in a single shot. Furthermore, the short x-ray pulse duration provided by this FEL prevents the blurring that is due to the heating associated with the absorption of radiation.

Several features are determined by using a 1-D analysis, showing that the laser and free electron interaction generates coherent XUV radiation. The simulation is based on: (1) the filling factor is one that is the electron beam and the laser beam completely overlap with each other; and (2) the laser beam is approximated by a square pulse.

Thus, the present analysis in one aspect is based on Gover's work. By way of background, refer to Gover, IEEE Journal of Quantum Electronics, Vol. QE-17, No. 3, July 1981, incorporated herein by reference in its entirety. The present analysis is developed immediately below and assumes a square uniform energy distribution and determines the longitudinal plasma susceptibility of the electron-beam propagating in the free space, which leads to determination of the collective gain in the free electron and laser interactions. This is a simple 1-D model and the inclusion of the transverse emittance is included.

Gain Theory—Based on Gover, it was found that the Laplace transformation of the collective gain is given by Equations (1) and (2).

Xp ($\omega/s$) is the longitudinal plasma susceptibility of an electron-beam propagating in the free space. It is defined by Equation (3).

$g^{(0)}$ is the canonical momentum distribution function of the electron beam and $v_z$ is the electron longitudinal velocity component. K is the coupling parameter. In the case of the free electron and laser interaction, the coupling parameter is given by Gover as per Equation (4).

$A_e$ is the electron-beam cross section area. $A_g$ is the effective cross section area of the electromagnetic mode. Together, $A_e/A_g$ is defined as "relative power" factor (filling factor), which we assume to be 1 in the calculations just to simply the situation.

According to Gover, the susceptibility function $x(\omega/s)$ (Equation (3)) can be defined by more familiar functions and parameters. The distribution function $g^{(0)}(p)$ can be expressed by normalized distribution function of a single variable. See Equation (5).

$n_0$ is the electron density, $p_{zth}$ is the longitudinal momentum spread and $p_{0z}$ is the average electron momentum in the longitudinal direction. See Equation (6).

$P_{0\perp}$ is the amplitude of the quiver momentum along the transverse direction. The axial average velocity can be calculated using $v_{0z}=p_{0z}/(\gamma_{0m})$. And $\gamma_{0z}$ can be calculated using the formula as per Equation (7).

Therefore, the plasma susceptibility can be re-written as per Equations 8-13.

$E_{zth}$ is the longitudinal kinetic energy spread of the electron beam.

Usually the Maxmillian distribution is used to approximate the real electron distribution. In that case, we will have to solve a transcendental fourth polynomial equation, which means we have four waves not three. To simplify the calculation, we instead use a square distribution and make the calculation easier.

Obtaining the electron beam susceptibility, the Laplace transformation of the gain will be given by the gain-dispersion relation (Equation (1)). When $\bar{a}(s)$ is inverse, Laplace transformed, the power gain will be given by Equation (14).

The operating wavelength is determined when the denominator in Equation (1) vanishes, which is also called the "dispersion equation."

Plasma Susceptibility Of The Electron Beam With A Square Distribution—Assume the normalized longitudinal momentum spread as a square uniform distribution; i.e., as per Equations (15) and then (16) and (17) pertain. Use the fact that $x_2-x_1\equiv 1$. Substitute G'($\zeta$) and s+$ik_0$ into Equation (8) and Equation (18) pertains where $r\equiv v'_{zth}/v_{0z}$, $\zeta$ is defined in Equation (10), $\omega'_p$ is defined by Equation (12) and $v'_{zth}$ is defined in Equation (13).

Further use definitions from Gover, as per Equations (19)-(22).

By using these definitions, Equations (23) and (24) result.

Substitute Equations (23) and (24) into Equation (8) and Equation (25) results.

Once the electron beam susceptibility is obtained, plug Equation (25) into Equation (1) to get the Laplace transformation of the amplitude gain as per Equation (26). Then Equations (27) and (28) result, where Q=$k\theta^2_p$. To get the real gain, carry out the inverse Laplace transformation. This can actually be completed by using Fourier transformation. See Equation (29). However, this could also be done by using the residue theorem. This will give Equation (39), where $A_j$ are the residues of Equation (27). Note that all the above derivations $\omega$ shall be replaced by $\omega-\omega_0$, where $\omega_0$ is the laser's frequency. This is just a matter of notations used by Gover.

Numerical Solutions—In order to do this, it is necessary to consider the kinematics of the electrons in the laser field. The electrons quivering momentum along the transverse direction is approximated by $eE_0/\omega_0$, and use Equation (6) to calculate the average longitudinal momentum, which will further be used to calculate the $\gamma_{0z}$. Here, use an alternative way to do this and still follow the definitions of Gover. The average longitudinal momentum $p_{0z}$ of an electron with an initial velocity of $\beta_{0z}$ can be directly given by Equations (31) and (32), wherein the overhead bar means the average along one electron motion period and $\gamma_{ini}$ in the initial relativity factor before the electron enters the interaction region with a velocity of $\beta_{z0}$. The longitudinal average velocity is then calculated using the relation $v_{0z}=p_{0z}/(\gamma_{0m})$, which will be used again the calculate $\gamma_{0z}$ using the definition $\gamma_{0z}\equiv(1-\beta^2_{0z})^{-1/2}$.

The $x_1$ and $x_2$ in the previous part are yet to be determined. This can be done by finding out the high momentum and low momentum of the electron beam with a longitudinal kinetic energy spread of $E_{zth}$.

In the limit of the zero energy spread and zero emittance, to estimate the maximum radiative energy extraction efficiency, use Equations (33) and (34), where $\delta k$ is the pole of the dispersion relation.

Experimental data shows that up to $1.36\times10^{11}$ electrons/MeV/sr can be accelerated with energy 2 MeV/sr using a 50-TW laser with 1-ps pulse duration. In a separate experiment, $9.7\times10^8$ electrons/MeV/sr were produced using a 10-TW power laser with 0.4-ps pulse duration. Lastly, $9.13\times10^9$/MeV were reported using a 30-TW power laser with 0.03-ps pulse duration. Using the best result, $1.36.10^{11}$ electrons/MeV/steradian and assuming a 1 steradian divergence angle, then there are $5\times10^9$ electrons in a 1-% energy bandwidth. Note that 1% conversion efficiency, from laser energy to electron energy, has been reported recently from thin-film solid target experiments. As discussed above, those electrons with energies outside of this 1-% energy bandwidth can easily be filtered out by means of magnets.

Listed in the Table 1 are the laser and electron beam parameters (conservatively assuming $10^9$ electrons in a 1 ps pulse focused to a 10-μm spot), and assuming the electron beam has zero energy spread and transverse emittance.

Figure 10:
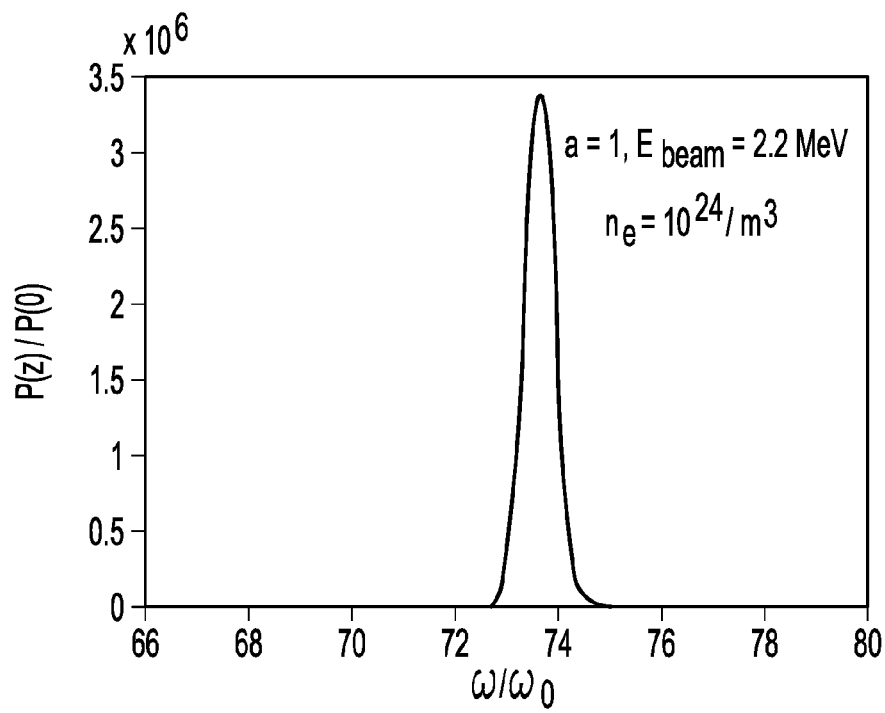
FIG. 10 shows a graph of exponential gain in XUV regime.

Because the electrons get bunched, and therefore emit coherent radiation, the power gain of the radiation after the interaction is exponential as show in FIG. 10. From FIG. 10, the x-axis shows that the largest gain is designed at around 74 times the laser frequency, which means it lases at a wavelength of 13.5 nm.

Figure 11:
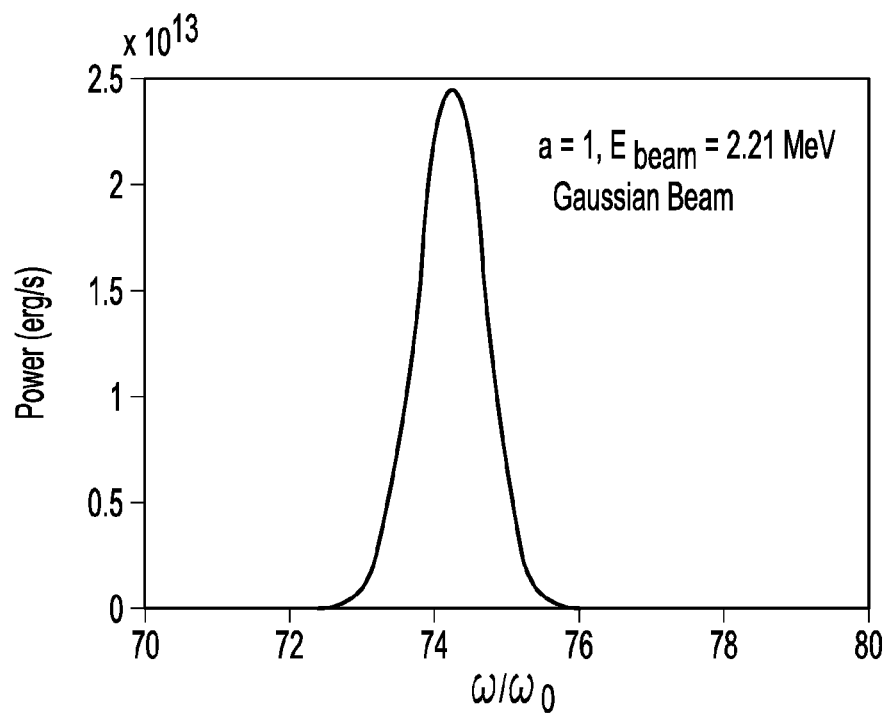
FIG. 11 shows a graph of incoherent XUV source.

A more practical example is when the beam has finite energy spread and emittance. First, consider the single particle calculation or incoherent Thomson scattering. To simplify the analysis, consider only the first harmonic of the Doppler-shifted frequency. Because normalized vector potential of the laser field, a, is around 1, the linear effects dominate and therefore the assumption is justified. If the electron bunch has $10^9$ particles and they follow a Gaussian distribution with an average energy of $E_0$=2.21 MeV and a standard deviation of $\sigma=E_0\times1.5\%/2$ so that 95% of the electrons will fall into the 3% energy spread, a spectrum that peaks around 13.5 nm is achieved, as in FIG. 11. The laser wavelength used here is 1 μm. When finite number of laser optical period is considered, there is another broadening effect of 1/N that should be included, where N is the number of optical cycles.

Turning to the collective gain, Table 2 gives the beam parameters. By assuming a square longitudinal energy spread, the impact of the longitudinal energy spread on the collective gain is derived.

Figure 12:
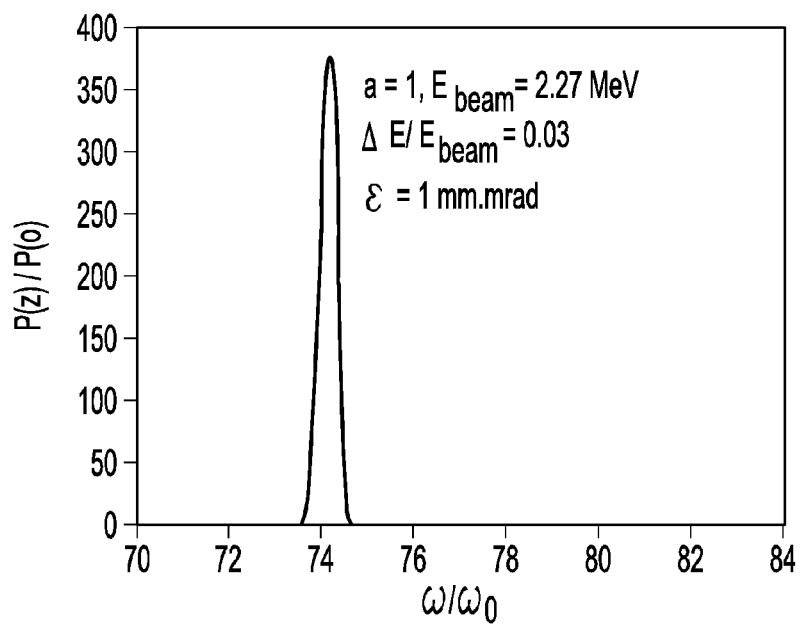
FIG. 12 shows a graph of collective gain with finite energy spread and transverse emittance.

Because the collective gain theory used is an 1-D model, it can not systematically include and transverse emittance into the calculation. However, the transverse emittance is converted into the longitudinal energy spread and treated the same way as is done for the original kinetic energy spread, by adding these two spreads quadratically. FIG. 12 gives the gain curve using the parameters in Table 2. It shows that even with a relatively high energy spread and high transverse emittance, reasonable gain in the XUV regime is achieved.

To compare the current calculations with the conventional light sources, one needs to estimate the brightness for both the incoherent and coherent radiations. Brightness or brilliance is usually defined as shown in Equation (101).

The spectral flux is the number of photons per unit time in a given bandwidth as shown in Equation (102) where I is the electron beam current, $(\Delta\omega/\omega)$ is usually taken as 0.1% and needs to be $<<1/N$. For a gaussian beam, the transverse phase space area is given in Equation (103) where certain parameters of Equation (103) are as in Equations (104)-(107). The brightness becomes as represented by B in Equation (8) and the unit of the brightness is: # of photons/ (mm²·mrad·s·0.1% BW).

Then, the parameters listed in Table 2 are to estimate the brightness of the incoherent radiation and the results are shown in Table 3.

To calculate I/e, Equation (109) is used. The analysis also used the fact that for the incoherent radiation the transverse phase space is predominantly given by the electron beam's emittance.

However, given the obtaining of the coherent radiation, the brightness can be greatly enhanced by two factors:

Transverse Coherence—Because the electron beam is now completely coherent transversely, the phase space will be given, in this case, mostly by $(\lambda_1/4\pi)^2$. For the radiation at $\lambda_1=13$ nm, compared to the incoherent case, this will give an increase factor as per Equation (110).

Temporal Coherence—As shown before, because the electron beam is bunched, all electron emit coherently. This is the usual factor of $N^2_e$. Using the number given by the collective effects as in FIG. 12, it will give another increase factor of 400.

Relative to the saturation efficiency, to estimate the maximum radiative energy extraction efficiency, we use Equation (111), where $\eta$ is defined as in Equation (112). For the case listed in Table 1, the maximum saturation efficiency, according to Equation (111), is 0.61%. For another wavelength of interest in lithography, 90 nm, it is 1.65%. With the tapering of the wiggler, the saturation efficiency of an FEL can be increased to 3.5%. Here, the same is done by using a chirped laser pulse for the amplifier pump. By doing so, a similar efficiency, 3.5%, is achievable with a laser-based wiggler. For $\eta_e=10^9$ electrons per bunch, the maximum photon energy is extracted from this amplification process, assuming is $\eta_0=0.61\%$, and per Equation (113). If the number of electrons within the requisite 1% energy range is $5\times10^9$, which has already been achieved experimentally, then $E=10^{-5}$ J. This corresponds to a conversion efficiency from laser energy to XUV energy $(\eta_1)$ of $\eta_1=4\times10^{-7}$, since 25 J of laser energy was used to produce the electron beam. Another important application of a table-top FEL is for metrology or microscopy, the requirements of which are much less stringent than those of lithography. In this case, a lower power coherent source of x-rays is required in order to characterize the nanometer scale features that are created either by lithography or by any of the other means being used in the field of nanotechnology. The laser, electron beam and x-ray parameters required for such a device can be met with current technology. An example set of parameters for this application are given in Table 4.

Note that a seed pulse of 13 nm wavelength is able to be generated by means of harmonic generation in clusters with an efficiency of $\sim10^{-4}$, although it is unclear what is the angular distribution of this radiation. Thus, even though the calculated gains given in the above examples, even in the case of finite electron beam energy spread and emittance, are sufficient to amplify a seed pulse to the level of the saturation efficiency of the amplifier, 0.54%, what limits the conversion efficiency to well below that limit is the relatively low energy stored in the electron beam, within the requisite energy bandwidth, as can be seen from Equation (113).

Figure 13:
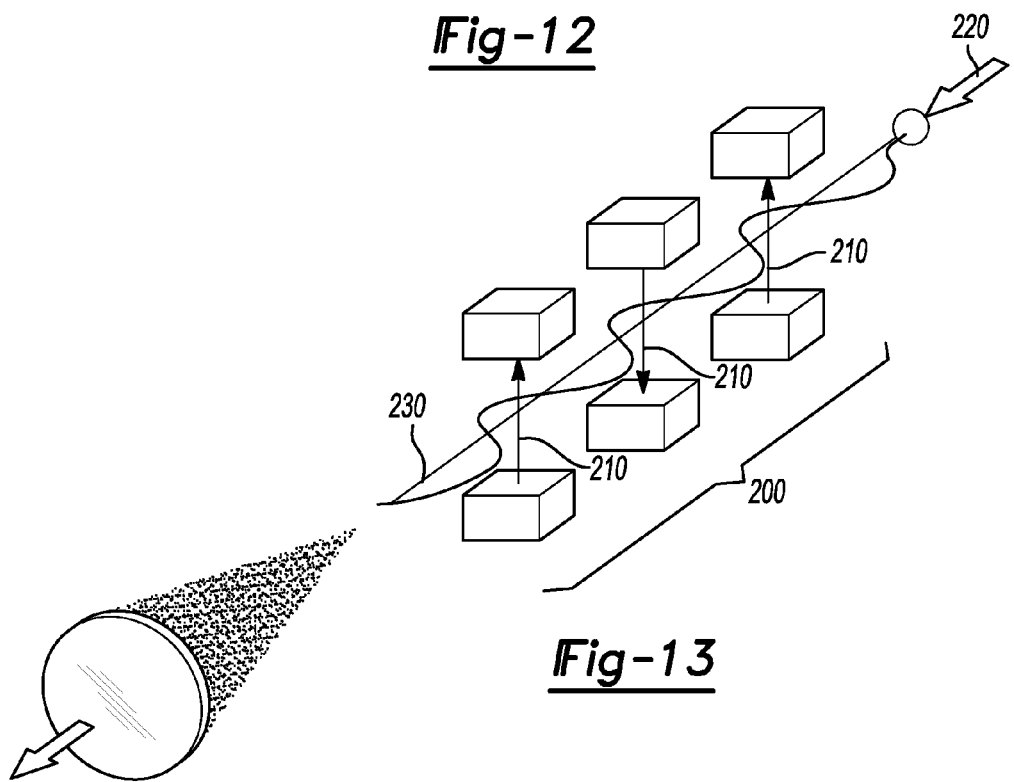
FIG. 13 is a schematic drawing illustrating the physical mechanism of a magnetostatic undulator.

In order to increase the energy stored in the electron beam, either the electron energy or the electron number needs to be increased. In the former case, a longer wavelength laser wiggler is required in order to reach a given final x-ray wavelength, because of the $\gamma^2$-scaling of the latter. For instance, the same given x-ray wavelength can be produced either by using a 10-μm-wavelength $CO_2$ laser for the wiggler or a 1-μm-wavelength glass-laser wiggler but with an electron-beam energy that is ten-times lower. The final energy of the x-ray beam is correspondingly ten-times larger in the former case. The stored energy is able to be increased even further, by another factor of ten, if a magnetostatic wiggler of mm wavelength were used with a 200-MeV energy laser-accelerated electron beam. In the case of a magnetostatic wiggler 200, shown in FIG. 13, the magnetic field 210 is pointed in a direction perpendicular to the motion of the electrons 220 but alternates in direction along the direction of the electron motion. The line designated as 230 represents electron motion that would occur without undulation or represents the average motion with undulation. From the vantage point of a relativistic electron, this appears equivalent to an oncoming electromagnetic wave, and thus all of the descriptions given earlier apply. The only important difference is that the wavelength is longer and so the same given x-ray radiation wavelength can be generated from a magnetostatic wiggler as from a laser wiggler, but from an electrom beam with a higher electron energy.

The number of electrons in a picosecond pulse might be increased—by operating at a higher plasma density—to the Alfven current $(17\beta\gamma$ kA), which corresponds to $10^{12}$ electrons in 1 ps. This corresponds to $\eta_1=2\times10^{-3}$ if all the electrons were put in the correct energy range by some form of injection, for instance. That is, in order to increase the number of electrons even further, the electron pulse duration would need to be increased. For XUV lithography, this conversion efficiency is comparable to xenon-cluster-based systems, which are expected to operate with an efficiency of 0.3%, when the difference between the solid angle of the emission and that subtended by the condenser lens is taken into consideration. With this conversion efficiency, a laser power 23 kW is required to deliver 70 W of inband power on the condenser lens. This is still an order of magnitude below the highest theoretical single-stage saturation efficiency for the FEL, 3.5%.

Such a high number of MeV-energy electrons per shot have been accelerated in experiments with a petawatt-peak-power laser incident on a solid-target, 1-mm Au: $2.5 \times 10^{13}$ electrons/shot in a beam with a temperature of 4 MeV or $\frac{2}{5} \times 10^{13}$/MeV/shot. Given that $4.7 \times 10^{12}$ of these electrons are put in a 1% energy range, but otherwise have ideal emittance properties, then an example set of parameters meeting the power requirements for lithography corresponds to this values as shown in Table 5. If the number of electrons were further reduced by a factor of ten, then the repetition rate would need to be increased by the same factor in order to achieve the same final x-ray power. Since the laser in this case had an energy of 500 J, this corresponds to an average power of 500 kW. It should be noted that this experiment was not done in an optimized parameter regime; if it were, a factor-of-ten reduction in the required laser power (to 50 kW) would be expected to result.

The relative compactness of laser-driven electrons accelerators and wigglers, compared with their conventional counterparts, renders them suitable for a new generation of free electron lasers. Here are shown various means of reducing the energy spread of laser-driven electron beams in order to enable their use for this purpose. The scaling of the conversion efficiency with various electron-beam parameters for x-ray wavelengths that are relevant to several important applications have been analyzed and demonstrated. Generally speaking, the current limitation on the achievable conversion efficiency, to levels well below the highest theoretical single-stage saturation efficiency for the FEL, $\eta_1 << \eta_0 = 3.5\%$, originates from the relatively low energy, within a narrow energy range, that is stored in current laser-driven electron beams. For the purpose of XUV lithography, the efficiency of a laser-driven FEL could, with improvements, rival that of xenon cluster sources, $\eta_1 = 0.3\%$, while eliminating the debris problem. Such improvements include injection of electrons into the laser-driven plasma waves, longer electron pulses, or the use of laser driven arc-discharge sources. For more advanced lithography using 1-nm x-rays, the all-laser-driven FEL, even with existing electron beam parameters, are thought to be able to produce much higher efficiency than any other compact source.

Those skilled in the art will appreciate the following variations within the scope of the invention for optimization of various features as described immediately below.

Optimization of the spatial and temporal overlap of the various laser and electron beams by: other magnetic field configurations for focusing and dispersion; feed back control of the laser or electron focusing optics combined with electron- and laser-beam position detectors; electrostatic and/or magnetostatic electron beam focusing; imaging of the spatial overlap by use of Thomson scattering; passing the beams through a pinhole; interference from a thin glass slide; ionization defocusing in a gas; nonlinear (two-photon) effects in optical media, such as harmonic generation; Schleiren photography; and/or imaging Thomson scattering produced by separate laser beams in a gas jet or back-filled chamber.

Optimization of the focus of either the pump or the scattering laser foci by focusing with a deformable mirror.

Optimization of the wiggler laser beam by: independent variation of the parameters of the various laser pulses; synchronization of independent laser systems, with different parameters, e.g., one laser for the production of the scattering beam, a separate laser for the electron beam generation and another laser for the harmonic generation; use of chirped laser pulses; and/or replace laser wiggler with magnetostatic wiggler.

Optimization of the electron beam parameters by: seeding of the density perturbation of the electron beam by variation of the plasma density and thus plasma-wave wavelength; pre-bunching the electron beam; variation of the gas-jet nozzle orifice; use slit gas jet; replace gas jet with thin-film solid target, using either front- or rear-side electron emission; replace gas jet with gas-filled capillary; replace or enhance accelerator with laser-triggered direct-current Marx-bank capacitive arc-discharge; replace gas jet with an accelerator based on the generation of electrons beams in a dense gas with a dielectric-barrier-discharge-based cathode; replace gas jet with capillary tube discharge; replace gas jet with preformed plasma from ablated solid target; variation of the electron beam energy; dual gas jet or gas jet stop to create a plasma density discontinuity to inject electrons; variation of the target density; variation of the target element; variation of the composite gas or solid; variation of the laser wavelength, pulse duration, chirp, contrast, energy, focal spot size; electron beam focusing by means of electrostatic lenses; optical injection; reduction of the electron beam emittance by means of laser scattering and radiative damping caused by the interaction of the beam with a separate laser beam, or by emittance selector; introduction of a correlated chirp on the electron beam and the use of chicane magnetostatic system in order to adjust its pulse duration; and/or increase of the repetition rate.

Optimization of the plasma wave by seeding of the plasma wave with another laser pulse shifted in frequency by: the plasma frequency; or replace single-pulse laser wakefield with a two-pulse laser beat-wave accelerator; optimization of the pulse duration of the pump laser beam by multiple laser pulses (RLPA); chirped laser pulses; and/or prescribed pre-pulse by variation of laser contrast.

Optimization of seed pulse by quasi phase matching by periodic plasma density modulation and/or quasi phase matching by periodic capillary structure modulation.

Optimization of pump lasers by use of a pulse stacker to lengthen the duration of the laser pulse on target and/or generation of shorter pump wavelengths of any of the pump lasers by means of harmonic generation in a nonlinear medium, such as a YAG crystal, using gas amplifiers, such as Excimer or Carbon-dioxide, or using chemical laser.

Even with existing electron-beam parameters, a laser-driven FEL, according to the invention, provides levels of brightness, coherence and collimation that are sufficient for protein structural analysis or nano-scale metrology and microscopy, and are comparable to, or exceed, those of third generation synchrotrons, while being far more compact and affordable. Unlike synchrotrons, they also have the potential to produce a sufficient number of x-rays in a single pulse, with a duration that is short enough, for the analysis of the protein structure before it is distorted by the absorption of radiation. Additionally, they are unique in being absolutely synchronized with a laser pulse, and thus can be used to study protein dynamics without jitter. Last, their superior coherence properties leads to better phase information, which correspondingly leads to improved interpretation of protein structure.

The description of the invention is merely exemplary in nature and, thus, variations that do not depart from the gist of the invention are intended to be within the scope of the invention. Such variations are not to be regarded as a departure from the spirit and scope of the invention.

Tables 1-3

TABLE 1

Collective effects at different lasing wavelengthes with electron's number density of $1.0 \times 10^{21}/m^3$.

| | | Radiation Wavelength | | |
|---|---|---|---|---|
| | | 90 nm | 13.5 nm | 1 nm |
| Beam Properties | Energy (MeV) | 0.575 | 2.240 | 9.450 |
| | Energy spread | 0 | 0 | 0 |
| | Beam current (A) | $3.4 \times 10^2$ | $3.8 \times 10^2$ | $3.8 \times 10^2$ |
| | Emittance (m · rad) | 0 | 0 | 0 |
| | #/bunch | $4.7 \times 10^9$ | $4.7 \times 10^9$ | $4.7 \times 10^9$ |
| | Bunch length (μm) | 600 | 600 | 600 |
| | Beam radius (μm) | 50 | 50 | 50 |
| | Number density (#/m³) | $1.0 \times 10^{21}$ | $1.0 \times 10^{21}$ | $1.0 \times 10^{21}$ |
| Gain Parameters | Seeding (W) | 20 | 20 | 20 |
| | Efficiency | 0.16% | 0.06% | 0.03% |
| | Saturation power (MW) | 0.32 | 0.52 | 1.03 |
| | Gain | 159 | 260 | 516 |
| | Saturation length (μm) | 137 | 401 | 2525 |
| Avg. Parameters | Repetition rate (Hz) | 1000 | 1000 | 1000 |
| | Avg. power (mW) | 0.64 | 1.04 | 2.06 |

TABLE 2

Collective effects at different lasing wavelengthes with electron's number density of $1.0 \times 10^{24}/m^3$.

| | | Radiation Wavelength | | |
|---|---|---|---|---|
| | | 90 nm | 13.5 nm | 1 nm |
| Beam Properties | Energy (MeV) | 0.590 | 2.240 | 9.450 |
| | Energy spread | 0 | 0 | 0 |
| | Beam current (A) | $3.4 \times 10^5$ | $3.8 \times 10^5$ | $3.8 \times 10^5$ |
| | Emittance (m · rad) | 0 | 0 | 0 |
| | #/bunch | $4.7 \times 10^{12}$ | $4.7 \times 10^{12}$ | $4.7 \times 10^{12}$ |
| | Bunch length (μm) | 600 | 600 | 600 |
| | Beam radius (μm) | 50 | 50 | 50 |
| | Number density (#/m³) | $1.0 \times 10^{24}$ | $1.0 \times 10^{24}$ | $1.0 \times 10^{24}$ |
| Gain Parameters | Seeding (W) | 20 | 20 | 20 |
| | Efficiency | 1.65% | 0.54% | 0.13% |
| | Saturation power (GW) | 3.30 | 4.57 | 4.83 |
| | Gain | $1.7 \times 10^6$ | $2.4 \times 10^6$ | $2.4 \times 10^6$ |
| | Saturation length (μm) | 32 | 89 | 328 |
| Avg. Parameters | Repetition rate (Hz) | 1000 | 1000 | 1000 |
| | Avg. power (W) | 6.60 | 9.14 | 9.66 |

TABLE 3

Brightness for the incoherent source

| N | 100 |
|---|---|
| I/e(#/s) | $2.36 \times 10^{22}$ |
| ε(mm · mrad) | 1 |
| β | $4.36 \times 10^{17}$ |

Tables 4-5

TABLE 4

Laser-driven FEL parameters for a metrology or crystallography source, assuming current electron-beam emittance.

| | | 90 nm | 13.5 nm | 1 nm |
|---|---|---|---|---|
| Beam Properties | Energy (MeV) | 0.575 | 2.240 | 9.450 |
| | Energy spread | 1% | 1% | 1% |
| | Beam current (A) | $3.8 \times 10^7$ | $3.8 \times 10^7$ | $3.8 \times 10^7$ |
| | Emittance (m · rad) | 0 | 0 | 0 |
| | #/bunch | $4.7 \times 10^9$ | $4.7 \times 10^9$ | $4.7 \times 10^9$ |
| | Bunch length (μm) | 600 | 600 | 600 |
| | Beam radius (μm) | 50 | 50 | 50 |
| | Number density (#/m³) | $1.0 \times 10^{21}$ | $1.0 \times 10^{21}$ | $1.0 \times 10^{21}$ |
| Gain Parameters | Seeding (W) | 19 | 19 | 19 |
| | Efficiency | 11.9% | 3.1% | 0.67% |
| | Saturation power (TW) | 2.6 | 2.6 | 2.4 |
| | Gain | $\sim 10^6$ | $\sim 10^6$ | $\sim 10^6$ |
| | Saturation length (μm) | ~12 | ~31 | ~110 |
| Avg. Parameters | Repetition rate (Hz) | 10 | 10 | 10 |
| | Avg. power (μW) | 520 | 520 | 480 |

TABLE 5

Laser-driven FEL parameters for various lasing wavelengths of interest for lithography, assuming ideal electron-beam emittance.

| | | 90 nm | 13.5 nm | 1 nm |
|---|---|---|---|---|
| Beam Properties | Energy (MeV) | 0.575 | 2.240 | 9.450 |
| | Energy spread | 1% | 1% | 1% |
| | Beam current (A) | $3.8 \times 10^5$ | $3.8 \times 10^5$ | $3.8 \times 10^5$ |
| | Emittance (m · rad) | 0 | 0 | 0 |
| | #/bunch | $4.7 \times 10^{12}$ | $4.7 \times 10^{12}$ | $4.7 \times 10^{12}$ |
| | Bunch length (μm) | 600 | 600 | 600 |
| | Beam radius (μm) | 50 | 50 | 50 |
| | Number density (#/m³) | $1.0 \times 10^{24}$ | $1.0 \times 10^{24}$ | $1.0 \times 10^{24}$ |
| Gain Parameters | Seeding (W) | 19 | 19 | 19 |
| | Efficiency | 11.9% | 3.1% | 0.67% |
| | Saturation power (TW) | 2.6 | 2.6 | 2.4 |
| | Gain | $\sim 10^{11}$ | $\sim 10^{11}$ | $\sim 10^{11}$ |
| | Saturation length (μm) | ~12 | ~31 | ~110 |
| Avg. Parameters | Repetition rate (Hz) | 1000 | 1000 | 1000 |
| | Avg. power (W) | 52 | 52 | 48 |

Equations 1-15

$$\bar{a}(s) = \frac{1 + \chi(w, s + ik_0)/\epsilon}{(s - ik_{z0})[1 + \chi(w, s + ik_0)/\epsilon] - i\kappa\chi(w, s + ik_0)/\epsilon} \cdot a(0) \quad (1)$$

$$\chi(w, s + ik_0) \equiv \chi_p(w, s + ik_0). \quad (2)$$

$$\chi_p(w, s) \equiv -i\frac{e^2}{w} \int\int\int_{-\infty}^{+\infty} \frac{\partial g^{(0)}(p_x, p_y, p_z)/\partial p_z}{s - iw/v_z} dp_x dp_y dp_z. \quad (3)$$

-continued $$\kappa \equiv \frac{1}{2\pi}\left(\frac{eE_0}{mc^2}\right)^2 (1+\beta_{0z})^2 \frac{\gamma_{0z}^4}{\gamma_0^2}\frac{A_e}{A_g}\lambda. \tag{4}$$

$$g^{(0)}(p_z) \equiv \iint_{-\infty}^{+\infty} g^{(0)}(p_x, p_y, p_z)\,dp_x\,dp_y$$
$$\equiv \frac{n_0}{p_{zth}} \bar{g}\left(\frac{p_z - p_{0z}}{p_{zth}}\right). \tag{5}$$

$$p_{0z} = \sqrt{p_0^2 - p_{0\perp}^2}. \tag{6}$$

$$\gamma_{0z} = \frac{\gamma_0}{\sqrt{1+(p_{0\perp}/mc)^2}}. \tag{7}$$

$$\chi(w,s)/\epsilon = \frac{1}{2}\frac{k_D'^2}{s^2} G'(\zeta) \tag{8}$$

$$G(\zeta) \equiv \int_{-\infty}^{+\infty} \frac{\bar{g}(x)}{x-\zeta} dx \tag{9}$$

$$\zeta \equiv \frac{iw/s - v_{0z}}{v_{zth}'} \tag{10}$$

$$k_D'^2 \equiv 2\frac{w_p'^2}{v_{zth}'^2} \tag{11}$$

$$w_p'^2 \equiv \frac{w_p^2}{\gamma_0 \gamma_{0z}^2} = \frac{1}{\gamma_0 \gamma_{0z}^2}\frac{e^2 n_0}{m\epsilon} \tag{12}$$

$$v_{zth}' = \frac{p_{zth}}{\gamma_0 \gamma_{0z}^2 m} = \frac{E_{zth}}{\gamma_0 \gamma_{0z}^2 \beta_{0z} mc}. \tag{13}$$

$$\frac{P(z)}{P(0)} = \left|\frac{a(z)}{a(0)}\right|^2. \tag{14}$$

$$\bar{g}\left(\frac{p_z - p_{0z}}{p_{zth}}\right) = \bar{g}(x) = \begin{cases} 0, & -\infty < x < x_1; \\ 1, & x_1 \le x \le x_2; \\ 0, & x_2 < x < \infty. \end{cases} \tag{15}$$

Equations 16-25

$$G(\zeta) = \int_{-\infty}^{\infty} \frac{\bar{g}(x)}{x-\zeta} dx \tag{16}$$
$$= \int_{x_2}^{x_2} \frac{1}{x-\zeta} dx$$
$$= \ln\left(\frac{x_2-\zeta}{x_1-\zeta}\right)$$

$$G'(\zeta) = \frac{-1}{x_2-\zeta} + \frac{1}{x_1-\zeta} \tag{17}$$
$$= \frac{x_2 - x_1}{(x_2-\zeta)(x_1-\zeta)}$$
$$= \frac{1}{(x_2-\zeta)(x_1-\zeta)},$$

-continued $$\chi(w, s+ik_0)/\epsilon = \frac{w_p'^2}{v_{zth}'^2(s+ik_0)^2}\frac{1}{\left(x_2 - \dfrac{\dfrac{iw}{s+ik_0} - v_{0z}}{v_{zth}'}\right)\left(x_1 - \dfrac{\dfrac{iw}{s+ik_0} - v_{0z}}{v_{zth}'}\right)} \tag{18}$$

$$= \frac{w_p'^2}{v_{0z}^2}\frac{1}{\left\{\dfrac{x_2 r(s+ik_0) - }{\left[i\dfrac{w}{v_{0z}} - (s+ik_0)\right]}\right\}}\frac{1}{\left\{\dfrac{x_1 r(s+ik_0) - }{\left[i\dfrac{w}{v_{0z}} - (s+ik_0)\right]}\right\}},$$

$$\theta_p \equiv \frac{w_p'}{v_{0z}}; \tag{19}$$

$$s \equiv ik_{z0} + i\delta k; \tag{20}$$

$$\theta \equiv \frac{w}{v_{z0}} - k_0 - k_{z0}; \tag{21}$$

$$\theta_{th} \equiv \frac{w}{v_{0z}}\frac{v_{zth}'}{v_{0z}} = r\frac{w}{v_{0z}}. \tag{22}$$

$$r(s+ik_0) = (ik_{z0} + i\delta k + ik_0)r \tag{23}$$
$$= ir\left(\frac{w}{v_{0z}} - \theta + \delta k\right)$$
$$= i[\theta_{th} + (\delta k - \theta)r],$$

$$i\frac{w}{v_{0z}} - (s+ik_0) = (-\delta k + \theta)i. \tag{24}$$

$$\chi(w, s+ik_0)/\epsilon = \frac{-\theta_p^2}{\{x_2[(\delta k - \theta)r + \theta_{th}] - (\theta - \delta k)\}\{x_1[(\delta k - \theta)r + \theta_{th}] - (\theta - \delta k)\}} \tag{25}$$

Equations 26-34

$$\frac{\bar{a}(s)}{\bar{a}(0)} = \frac{1 + \chi(w, s+ik_0)/\epsilon}{(s-ik_{z0})[1+\chi(w,s+ik_0)/\epsilon] - i\kappa\chi(w,s+ik_0)/\epsilon}. \tag{26}$$

$$\frac{\bar{a}(s)}{\bar{a}(0)} = \frac{\Lambda - \theta_p^2}{i\delta k \Lambda + iQ} \tag{27}$$

$$\Lambda \equiv \{x_2[(\delta k - \theta)r + \theta_{th}] + (\delta k - \theta)\} \times \{x_1[(\delta k - \theta)r + \theta_{th}] + (\delta k - \theta)\}, \tag{28}$$

$$a(z) = \frac{1}{2\pi i}\int_{\gamma - i\infty}^{\gamma + i\infty} \bar{a}(s)e^{sz} ds. \tag{29}$$

$$\frac{a(z)}{a(0)} = \sum_{j=1}^{3} A_j e^{s_j z}, \tag{30}$$

$$p_{0z} = mc\overline{\gamma_0 \beta_z} = mc[\bar{\gamma}_0 - \gamma_{ini}(1-\beta_{z0})] \tag{31}$$

$$\bar{\gamma}_0 = \frac{1}{4}\frac{a^2}{\gamma_{ini}(1-\beta_{z0})} + \gamma_{ini}, \tag{32}$$

-continued $$\eta_0 = \frac{\beta_{0z}^3}{\beta_0^2}\gamma_{0z}^2(1+\gamma_0^{-1})\tilde{\eta}\frac{\lambda}{\pi}, \quad (33)$$

$$\tilde{\eta} \equiv \mathrm{Re}\delta k - \theta, \quad (34)$$

Equations 101-113

$$\mathcal{B} = \frac{\text{spectral flux}}{\text{transverse phase space area}}. \quad (101)$$

$$\alpha N(I/e)(\Delta w/w) \quad (102)$$

$$(2\pi)^2 \Sigma_x \Sigma_{x'} \Sigma_y \Sigma_{y'} \quad (103)$$

$$\sum_{x,y} = \sqrt{\sigma_{x,y}^2 + \sigma_r^2} \quad (104)$$

$$\sum_{x',y'} = \sqrt{\sigma_{x',y'}^2 + \sigma_{r'}^2} \quad (105)$$

$$\sigma_r \sim \frac{1}{4\pi}\sqrt{2\lambda_1 L} \quad (106)$$

$$\sigma_{r'} = \sqrt{\frac{\lambda_1}{2L}}. \quad (107)$$

$$\mathcal{B} = \frac{\alpha N(I/e)(\Delta w/w)}{4\pi^2 \Sigma_x \Sigma_{x'} \Sigma_y \Sigma_{y'}} \quad (108)$$

$$I/e = \frac{JS}{e} \quad (109)$$
$$= nv\pi r_b^2$$
$$\doteq 10^{24} \times 3 \times 10^8 \times \pi \times (5 \times 10^{-6})^2$$
$$= 2.36 \times 10^{22} \#/s.$$

$$\frac{\epsilon^2}{(\lambda_1/4\pi)^2} \approx \frac{1 \times 10^{-12} \times (4\pi)^2}{(13 \times 10^{-9})^2} \approx 6 \times 10^3; \quad (110)$$

$$\eta_0 = \frac{\beta_{0z}^3}{\beta_0^2}\gamma_{0z}^2(1+\gamma_0^{-1})\tilde{\eta}\frac{\lambda}{\pi}, \quad (111)$$

$$\tilde{\eta} \equiv \mathrm{Re}\delta k - \theta. \quad (112)$$

$$E_{photon} = \eta_0 n_e e V_{beam} \quad (113)$$
$$= 0.6\% \times 10^9 \times 1.6 \times 10^{-19} \times 2.2 \times 10^6$$
$$= 2.1 \times 10^{-6} J.$$

What is claimed is:

1. A method for generating electromagnetic radiation comprising:
producing free electrons;
selecting from said free electrons a group of electrons having an energy spread less than the remaining of said free electrons; and
undulating the group of free electrons with an undulator in an undulation zone, said undulator having an intensity sufficient to cause the emission of radiation from the group of electrons and causing the electron radiation to interact with radiation from the undulator to bunch the group of electrons, whereby such bunching generates further emission of radiation, wherein said selecting is accomplished by magnetic filtering and said magnetic filtering is accompanied by refocusing of the electron beam to the undulation zone.

2. A method of claim 1, wherein said producing of free electrons includes accelerating free electrons by means of an electron beam in a plasma.

3. A method of claim 1, wherein said producing of free electrons includes accelerating free electrons in a plasma.

4. A method of claim 1, wherein said producing of free electrons includes accelerating free electrons by means of a laser in a plasma.

5. A method of claim 4, wherein the accelerating is accomplished at least in part by a plasma wakefield.

6. A method of claim 5, wherein the accelerating is assisted by a direct-current (DC) electric field.

7. A method for generating electromagnetic radiation comprising:
producing free electrons;
selecting from said free electrons a group of electrons having an energy spread less than the remaining of said free electrons; and
undulating the group of free electrons with an undulator in an undulation zone, said undulator having an intensity sufficient to cause the emission of radiation from the group of electrons and causing the electron radiation to interact with radiation from the undulator to bunch the group of electrons, whereby such bunching generates further emission of radiation, wherein before said undulating, a beam of at least one pulse of electromagnetic radiation is produced; and wherein said free electrons and pulse of electromagnetic radiation coincide during said undulating to further enhance emission of radiation wherein said undulating constitutes a first-stage of undulating for said group of free electrons that is a first group of free electrons; a second group of free electrons is produced; and radiation from said first stage of undulating is added to a second stage of undulating comprising the undulating of the second group of free electrons.

8. A method of claim 1, wherein said undulating is accomplished by an electromagnetic laser wiggler.

9. A method of claim 1, wherein said undulating is accomplished by a magnetostatic undulator.

10. A method for generating electromagnetic radiation comprising:
producing free electrons;
selecting from said free electrons a group of electrons having an energy spread less than the remaining of said free electrons; and
undulating the group of free electrons with an undulator in an undulation zone, said undulator having an intensity sufficient to cause the emission of radiation from the group of electrons and causing the electron radiation to interact with radiation from the undulator to bunch the group of electrons, whereby such bunching generates further emission of radiation,
wherein said selecting is accomplished by preferentially accelerating those electrons in said group of electrons by means of optical injection, comprising generating a plasma and introducing additional laser pulses in the plasma, and wherein said preferential acceleration is accomplished by means of a sharp density discontinuity within the plasma.

11. The method of claim 1, wherein said selecting is accomplished by preferentially accelerating those electrons of said group.

12. The method of claim 1, wherein said emission of radiation is at a fundamental frequency.

13. The method for generating electromagnetic radiation comprising:
   producing free electrons;
   selecting from said free electrons a group of electrons having an energy spread less than the remaining of said free electrons; and
   undulating the group of free electrons with an undulator in an undulation zone, said undulator having an intensity sufficient to cause the emission of radiation from the group of electrons and causing the electron radiation to interact with radiation from the undulator to bunch the group of electrons, whereby such bunching generates further emission of radiation, wherein said emission of radiation comprises multiple frequencies that are multiples of a fundamental frequency.

14. The method of claim 13, wherein said multiple frequencies are generated by said undulator characterized by a field strength that is essentially non-sinusoidal.

15. The method for generating electromagnetic radiation comprising: producing a group of free electrons, undulating the group of free electrons and causing emission of radiation, wherein said emission of radiation comprises multiple frequencies that are multiples of a fundamental frequency.

16. The method of claim 15, wherein said multiple frequencies are generated by said undulator characterized by a field strength that is essentially non-sinusoidal.

17. A method for generating electromagnetic radiation comprising:
   generating a first group of free electrons and separately generating seed radiation; undulating the first group of free electrons in the presence of the seed radiation, thereby producing first amplified radiation; generating a second group of free electrons; and undulating the second group of free electrons and the first amplified radiation in a second undulator to produce second amplified radiation.

18. A method for generating electromagnetic radiation comprising:
   (a) generating a group of free electrons and separately generating seed radiation; undulating the group of free electrons in the presence of the seed radiation, thereby producing upstream amplified radiation; and
   (b) generating a further group of free electrons, and undulating the further group of free electrons and the upstream amplified radiation in a downstream undulator to produce a downstream amplified radiation.

19. The method of claim 18, wherein Step (b) is repeated for a multi-staged amplification of three stages or more.

20. A method for generating electromagnetic radiation comprising: producing a first group of free electrons having a first energy spread; undulating a second group of free electrons from among said first group of free electrons, said second group of free electrons having a second energy spread, said second energy spread being less than said first energy spread; where said undulator has an intensity sufficient to cause the emission of radiation from the second group of electrons and causes the electron radiation to interact with radiation from the undulator.

21. A method to generate electromagnetic radiation comprising: producing free electrons; arranging said free electrons into groups of free electrons having corresponding different energy ranges and spatially separating said groups; and undulating the groups of free electrons essentially simultaneously with respective undulators, said undulators each having an intensity sufficient to cause the emission of radiation from a respective one of said groups of free electrons and causing the electron radiation to interact with radiation from the undulator to bunch the electrons of a respective said group, whereby such bunching generates further emission of radiation of differing wavelengths corresponding to said groups respectively.

22. A method of generating electromagnetic radiation comprising: producing free electrons arranged in spatially separate groups of free electrons having essentially non-overlapping energy ranges; and undulating the spatially separate groups of free electrons essentially simultaneously, causing emission of radiation at various wavelengths.

23. The method of claim 1, wherein said producing of free electrons comprises photo-ionization of one or more selected from the group consisting of gas, liquid and solid.

24. The method of claim 2, wherein said plasma is produced by photo-ionization of one or more selected from the group consisting of gas, liquid and solid.

25. The method of claim 7, wherein said radiation from said first stage of undulating is collected and focused with x-ray optics before being added to said second stage of undulating.

26. The method of claim 25, wherein said focusing is by at least one selected from the group consisting of curved mirrors, zone plates and capillary fibers.

27. An apparatus for generating electromagnetic radiation comprising:
   (a) a source of a group of free electrons;
   (b) a source of seed radiation;
   (c) an undulator for undulating the group of free electrons in the presence of the seed radiation, thereby producing upstream amplified radiation;
   (d) a source of a further group of free electrons; and
   (e) a downstream undulator for undulating the further group of free electrons and the upstream amplified radiation to produce a downstream amplified radiation.

28. The apparatus of claim 27, having one or more additional downstream undulators for a multi-staged amplification of three stages or more.

29. The apparatus of claim 27 that comprises a collector for collecting said upstream radiation and x-ray optics for focusing said upstream radiation, said collector and x-ray optics arranged to direct said upstream radiation to said downstream undulator.

* * * * *

UNITED STATES PATENT AND TRADEMARK OFFICE
CERTIFICATE OF CORRECTION

PATENT NO. : 7,321,604 B2 Page 1 of 1
APPLICATION NO. : 10/752604
DATED : January 22, 2008
INVENTOR(S) : Umstadter et al.

It is certified that error appears in the above-identified patent and that said Letters Patent is hereby corrected as shown below:

Column 19, line 55 (Equation 16) " $= \int_{x_2}^{x_2} \frac{1}{x - \zeta} dx$ " should be -- $= \int_{x_1}^{x_2} \frac{1}{x - \zeta} dx$ --

Signed and Sealed this

Eighth Day of July, 2008

JON W. DUDAS
*Director of the United States Patent and Trademark Office*